US 6,605,053 B1

(12) United States Patent
Kamm et al.

(10) Patent No.: US 6,605,053 B1
(45) Date of Patent: Aug. 12, 2003

(54) CONDUIT DESIGNS AND RELATED METHODS FOR OPTIMAL FLOW CONTROL

(75) Inventors: Roger D. Kamm, Weston, MA (US); Eun Bo Shim, Kyungbuk (KR)

(73) Assignee: Percardia, Inc., Nashua, NH (US)

( * ) Notice: Subject to any disclaimer, the term of this patent is extended or adjusted under 35 U.S.C. 154(b) by 256 days.

(21) Appl. No.: 09/657,567

(22) Filed: Sep. 8, 2000

Related U.S. Application Data

(60) Provisional application No. 60/153,205, filed on Sep. 10, 1999.

(51) Int. Cl.$^7$ .............................. A61M 5/00; A61F 2/06
(52) U.S. Cl. ................................. 604/8; 604/9; 623/1.3
(58) Field of Search .................... 604/8, 9, 10, 129; 606/108; 623/1.3, 900, 903; 600/16; 128/898

(56) References Cited

U.S. PATENT DOCUMENTS 3,998,222 A * 12/1976 Shihata ..................... 604/175
4,503,568 A    3/1985 Madras (List continued on next page.)

FOREIGN PATENT DOCUMENTS

| EP | 0 732 008 | 9/1996 |
|---|---|---|
| EP | 0 824 903 | 2/1998 |
| EP | 0 876 803 | 11/1998 |
| EP | 0 903 123 | 3/1999 |
| EP | 0 904 745 | 3/1999 |
| EP | 0 955 017 | 11/1999 |
| EP | 0 955 019 | 11/1999 |
| EP | 0 962 194 | 12/1999 |
| EP | 1 020 166 A1 | 7/2000 |
| EP | 1 027 870 A1 | 8/2000 |
| EP | 1 097 676 | 5/2001 |
| EP | 1 166 721 A2 | 1/2002 |
| GB | 2316322 | 10/1998 |
| WO | 94/16629 | 8/1994 |
| WO | WO 96/25886 | 8/1996 |

OTHER PUBLICATIONS

US 6,331,185, 12/2001, Gambale et al. (withdrawn)

(List continued on next page.)

Primary Examiner—Alfred Basichas
(74) Attorney, Agent, or Firm—Finnegan, Henderson, Farabow, Garrett & Dunner, LLP

(57) ABSTRACT

A bypass conduit and related methods include implanting a bypass in the heart between a heart chamber and an at least partially occluded artery to directly flow blood from the chamber to the artery. The bypass conduit is configured to have a higher resistance to blood flow in a first direction than in a second direction without any active flow control mechanism. The bypass conduit may have a first end defining a first opening and a second end defining a second opening and a wall extending between the two ends that defines a lumen extending between the two openings. The ends and the wall of the conduit are configured to have a higher resistance to blood flow in a first direction than in a second direction. A method of bypassing an at least partially occluded artery includes determining a resistance to blood flow of the artery at a location of an at least partial occlusion and selecting a conduit having a configuration based on the resistance to blood flow of the artery at the location of the at least partial occlusion. The method further includes implanting the conduit in a heart wall between the heart chamber and the artery downstream of the at least partial occlusion to directly flow blood between the chamber and the artery.

42 Claims, 28 Drawing Sheets

U.S. PATENT DOCUMENTS

| | | | |
|---|---|---|---|
| 4,733,665 A | 3/1988 | Palmaz | |
| 4,769,029 A | 9/1988 | Patel | |
| 4,995,857 A | 2/1991 | Arnold | |
| 5,035,702 A | 7/1991 | Tahei | |
| 5,135,467 A | 8/1992 | Citron | |
| 5,193,546 A | 3/1993 | Shaknovich | |
| 5,258,008 A | 11/1993 | Wilk | |
| 5,282,860 A | 2/1994 | Matsuno et al. | |
| 5,287,861 A | 2/1994 | Wilk | |
| 5,330,486 A | 7/1994 | Wilk | |
| 5,344,426 A | 9/1994 | Lau et al. | |
| 5,385,541 A | 1/1995 | Kirsch et al. | |
| 5,409,019 A | 4/1995 | Wilk | |
| 5,423,744 A | 6/1995 | Gencheff et al. | |
| 5,423,851 A | 6/1995 | Samuels | |
| 5,429,144 A | 7/1995 | Wilk | |
| 5,443,497 A * | 8/1995 | Venbrux | 604/8 |
| 5,452,733 A | 9/1995 | Sterman et al. | |
| 5,456,712 A | 10/1995 | Maginot | |
| 5,456,714 A | 10/1995 | Owen | |
| 5,470,320 A | 11/1995 | Tiefenbrun et al. | |
| 5,527,337 A | 6/1996 | Stack et al. | |
| 5,571,167 A | 11/1996 | Maginot | |
| 5,578,075 A | 11/1996 | Dayton | |
| 5,593,434 A | 1/1997 | Williams | |
| 5,609,626 A | 3/1997 | Quijano et al. | |
| 5,618,299 A | 4/1997 | Khosravi et al. | |
| 5,655,548 A | 8/1997 | Nelson et al. | |
| 5,662,124 A | 9/1997 | Wilk | |
| 5,662,711 A * | 9/1997 | Douglas | 604/9 |
| 5,676,670 A | 10/1997 | Kim | |
| 5,695,504 A | 12/1997 | Gifford, III et al. | |
| 5,702,412 A | 12/1997 | Popov et al. | |
| 5,746,709 A | 5/1998 | Rom et al. | |
| 5,755,682 A * | 5/1998 | Knudson et al. | 604/8 |
| 5,758,663 A | 6/1998 | Wilk et al. | |
| 5,797,933 A | 8/1998 | Snow et al. | |
| 5,810,836 A | 9/1998 | Hussein et al. | |
| 5,817,113 A | 10/1998 | Gifford, III et al. | |
| 5,824,038 A | 10/1998 | Wall | |
| 5,824,071 A | 10/1998 | Nelson et al. | |
| 5,830,222 A | 11/1998 | Makower | |
| 5,843,163 A | 12/1998 | Wall | |
| 5,851,232 A | 12/1998 | Lois | |
| 5,855,597 A | 1/1999 | Jayaraman | |
| 5,861,026 A * | 1/1999 | Harris et al. | 604/8 |
| 5,865,723 A | 2/1999 | Love | |
| 5,875,782 A | 3/1999 | Ferrari et al. | |
| 5,876,419 A | 3/1999 | Carpenter et al. | |
| 5,878,751 A | 3/1999 | Hussein et al. | |
| 5,904,697 A | 5/1999 | Gifford, III et al. | |
| 5,908,028 A | 6/1999 | Wilk | |
| 5,908,029 A | 6/1999 | Knudson et al. | |
| 5,922,022 A | 7/1999 | Nash et al. | |
| 5,935,119 A | 8/1999 | Guy et al. | |
| 5,935,161 A | 8/1999 | Robinson et al. | |
| 5,935,162 A | 8/1999 | Dang | |
| 5,944,019 A | 8/1999 | Knudson et al. | |
| 5,961,548 A | 10/1999 | Shmulewitz | |
| 5,968,093 A | 10/1999 | Kranz | |
| 5,971,993 A | 10/1999 | Hussein et al. | |
| 5,976,159 A | 11/1999 | Bolduc et al. | |
| 5,976,169 A | 11/1999 | Imran | |
| 5,976,178 A | 11/1999 | Goldsteen et al. | |
| 5,976,181 A | 11/1999 | Whelan et al. | |
| 5,976,182 A | 11/1999 | Cox | |
| 5,976,192 A | 11/1999 | McIntyre et al. | |
| 5,976,650 A | 11/1999 | Campbell et al. | |
| 5,979,455 A | 11/1999 | Maginot | |
| 5,980,548 A | 11/1999 | Evans et al. | |
| 5,980,551 A | 11/1999 | Summers et al. | |
| 5,980,552 A | 11/1999 | Pinchasik et al. | |
| 5,980,553 A | 11/1999 | Gray et al. | |
| 5,980,566 A | 11/1999 | Aita et al. | |
| 5,984,955 A | 11/1999 | Wisselink | |
| 5,984,956 A | 11/1999 | Tweden et al. | |
| 5,984,963 A | 11/1999 | Ryan et al. | |
| 5,984,965 A | 11/1999 | Knapp et al. | |
| 5,989,207 A | 11/1999 | Hughes | |
| 5,989,276 A | 11/1999 | Houser et al. | |
| 5,989,287 A | 11/1999 | Yang et al. | |
| 5,993,468 A | 11/1999 | Rygaard | |
| 5,993,481 A | 11/1999 | Marcade et al. | |
| 5,993,482 A | 11/1999 | Chuter | |
| 5,997,563 A | 12/1999 | Kretiers | |
| 5,997,573 A | 12/1999 | Quijano et al. | |
| 6,001,123 A | 12/1999 | Lau | |
| 6,004,261 A | 12/1999 | Sinofsky et al. | |
| 6,004,347 A | 12/1999 | McNamara et al. | |
| 6,004,348 A | 12/1999 | Banas et al. | |
| 6,007,544 A | 12/1999 | Kim | |
| 6,007,575 A | 12/1999 | Samuels | |
| 6,007,576 A | 12/1999 | McClellan | |
| 6,010,530 A | 1/2000 | Goicoechea | |
| 6,017,365 A | 1/2000 | Von Oepen | |
| 6,026,814 A | 2/2000 | LaFontaine et al. | |
| 6,029,672 A | 2/2000 | Vanney et al. | |
| 6,035,856 A | 3/2000 | LaFontaine et al. | |
| 6,045,565 A | 4/2000 | Ellis et al. | |
| 6,053,911 A | 4/2000 | Ryan et al. | |
| 6,053,924 A | 4/2000 | Hussein | |
| 6,053,942 A | 4/2000 | Eno et al. | |
| 6,067,988 A | 5/2000 | Mueller | |
| 6,068,638 A | 5/2000 | Makower | |
| 6,071,292 A | 6/2000 | Makower et al. | |
| 6,076,529 A | 6/2000 | Vanney et al. | |
| 6,080,163 A | 6/2000 | Hussein et al. | |
| 6,093,166 A | 7/2000 | Knudson et al. | |
| 6,095,997 A | 8/2000 | French et al. | |
| 6,102,941 A | 8/2000 | Tweden et al. | |
| 6,106,538 A | 8/2000 | Shiber | |
| 6,110,201 A | 8/2000 | Quijano et al. | |
| 6,113,630 A | 9/2000 | Vanney et al. | |
| 6,113,823 A | 9/2000 | Eno | |
| 6,117,165 A | 9/2000 | Becker | |
| 6,123,682 A | 9/2000 | Knudson et al. | |
| 6,126,649 A | 10/2000 | Van Tassel et al. | |
| 6,139,541 A | 10/2000 | Vanney et al. | |
| 6,152,141 A | 11/2000 | Stevens et al. | |
| 6,155,264 A | 12/2000 | Ressemann et al. | |
| 6,159,225 A | 12/2000 | Makower | |
| 6,162,245 A | 12/2000 | Jayaraman | |
| 6,182,668 B1 | 2/2001 | Tweden et al. | |
| 6,186,972 B1 | 2/2001 | Nelson et al. | |
| 6,187,034 B1 | 2/2001 | Frantzen | |
| 6,190,353 B1 | 2/2001 | Makower et al. | |
| 6,193,726 B1 | 2/2001 | Vanney | |
| D438,618 S | 3/2001 | Solem | |
| 6,196,230 B1 | 3/2001 | Hall et al. | |
| 6,197,050 B1 | 3/2001 | Eno et al. | |
| 6,203,556 B1 | 3/2001 | Evans et al. | |
| 6,213,126 B1 | 4/2001 | LaFontaine et al. | |
| 6,214,041 B1 | 4/2001 | Tweden et al. | |
| 6,223,752 B1 | 5/2001 | Vanney et al. | |
| 6,231,587 B1 | 5/2001 | Makower | |
| 6,237,607 B1 | 5/2001 | Vanney et al. | |
| 6,238,406 B1 | 5/2001 | Ellis et al. | |
| 6,245,102 B1 | 6/2001 | Jayaraman | |
| 6,250,305 B1 | 6/2001 | Tweden | |
| 6,253,768 B1 | 7/2001 | Wilk | |
| 6,253,769 B1 | 7/2001 | LaFontaine et al. | |

| | | | | | |
|---|---|---|---|---|---|
| 6,254,564 B1 | 7/2001 | Wilk et al. | 2002/0123698 A1 | 9/2002 | Garibotto et al. |
| 6,258,119 B1 | 7/2001 | Hussein et al. | 2002/0144696 A1 | 10/2002 | Sharkawy et al. |
| 6,261,304 B1 | 7/2001 | Hall et al. | 2002/0161424 A1 | 10/2002 | Rapacki et al. |
| 6,283,951 B1 | 9/2001 | Flaherty et al. | 2002/0165479 A1 | 11/2002 | Wilk |
| 6,283,983 B1 | 9/2001 | Makower et al. | 2002/0165606 A1 | 11/2002 | Wolf et al. |
| 6,287,317 B1 | 9/2001 | Makower et al. | | | |

FOREIGN PATENT DOCUMENTS

| | | |
|---|---|---|
| 6,290,719 B1 | 9/2001 | Garberoglio |
| 6,290,728 B1 | 9/2001 | Phelps et al. |
| 6,293,955 B1 | 9/2001 | Houser et al. |
| 6,302,875 B1 | 10/2001 | Makower |
| 6,302,892 B1 | 10/2001 | Wilk |
| 6,306,125 B1 | 10/2001 | Parker et al. |
| 6,330,884 B1 | 12/2001 | Kim |
| 6,350,248 B1 | 2/2002 | Knudson et al. |
| 6,361,519 B1 | 3/2002 | Knudson et al. |
| 6,363,938 B2 | 4/2002 | Saadat et al. |
| 6,363,939 B1 | 4/2002 | Wilk |
| 6,375,615 B1 | 4/2002 | Flaherty et al. |
| 6,379,319 B1 | 4/2002 | Garibotto et al. |
| 6,387,119 B2 * | 5/2002 | Wolf et al. ................ 128/898 |
| 6,390,098 B1 | 5/2002 | LaFontaine et al. |
| 6,406,488 B1 | 6/2002 | Tweden et al. |
| 6,406,491 B1 | 6/2002 | Vanney |
| 6,409,697 B2 | 6/2002 | Eno et al. |
| 6,409,751 B1 | 6/2002 | Hall et al. |
| 6,423,089 B1 | 7/2002 | Gingras et al. |
| 6,432,126 B1 | 8/2002 | Gambale et al. |
| 6,432,127 B1 | 8/2002 | Kim et al. |
| 6,432,132 B1 | 8/2002 | Cottone et al. |
| 6,443,158 B1 | 9/2002 | LaFontaine et al. |
| 6,447,522 B2 | 9/2002 | Gambale et al. |
| 6,447,539 B1 | 9/2002 | Nelson et al. |
| 6,454,760 B2 | 9/2002 | Vanney |
| 6,454,794 B1 | 9/2002 | Knudson et al. |
| 6,458,323 B1 | 10/2002 | Boekstegers |
| 2001/0004683 A1 | 6/2001 | Gamble et al. |
| 2001/0004690 A1 | 6/2001 | Gamble et al. |
| 2001/0004699 A1 | 6/2001 | Gittingss et al. |
| 2001/0008969 A1 | 7/2001 | Evans et al. |
| 2001/0012948 A1 | 8/2001 | Vanney |
| 2001/0014813 A1 | 8/2001 | Saadat et al. |
| 2001/0016700 A1 | 8/2001 | Eno et al. |
| 2001/0025436 A1 | 10/2001 | Foley |
| 2001/0027287 A1 | 10/2001 | Shmulewitz et al. |
| 2001/0034547 A1 | 10/2001 | Hall et al. |
| 2001/0037117 A1 | 11/2001 | Gamble et al. |
| 2001/0037149 A1 | 11/2001 | Wilk |
| 2001/0039426 A1 | 11/2001 | Makower et al. |
| 2001/0039445 A1 | 11/2001 | Hall et al. |
| 2001/0041902 A1 | 11/2001 | Lepulu et al. |
| 2001/0047165 A1 | 11/2001 | Makower et al. |
| 2001/0053932 A1 | 12/2001 | Phelps et al. |
| 2002/0002349 A1 | 1/2002 | Flaherty et al. |
| 2002/0004662 A1 | 1/2002 | Wilk |
| 2002/0007138 A1 | 1/2002 | Wilk et al. |
| 2002/0029079 A1 | 3/2002 | Kim et al. |
| 2002/0032476 A1 | 3/2002 | Gambale et al. |
| 2002/0033180 A1 | 3/2002 | Solem |
| 2002/0038100 A1 | 3/2002 | Okada |
| 2002/0049486 A1 | 4/2002 | Knudson et al. |
| 2002/0052637 A1 | 5/2002 | Houser et al. |
| 2002/0058897 A1 | 5/2002 | Renati |
| 2002/0062146 A1 | 5/2002 | Makower et al. |
| 2002/0065478 A1 | 5/2002 | Knudson et al. |
| 2002/0072699 A1 | 6/2002 | Knudson et al. |
| 2002/0077566 A1 | 6/2002 | Laroya et al. |
| 2002/0092535 A1 | 7/2002 | Wilk |
| 2002/0095111 A1 | 7/2002 | Tweden et al. |
| 2002/0100484 A1 | 8/2002 | Hall et al. |
| 2002/0111669 A1 | 8/2002 | Pazienza et al. |
| 2002/0111672 A1 | 8/2002 | Kim et al. |

| | | |
|---|---|---|
| WO | 97/13463 | 4/1997 |
| WO | 97/13471 | 4/1997 |
| WO | WO 97/18768 | 5/1997 |
| WO | 97/27893 | 8/1997 |
| WO | 97/27897 | 8/1997 |
| WO | 97/27898 | 8/1997 |
| WO | WO 97/31590 | 9/1997 |
| WO | 97/32551 | 9/1997 |
| WO | 97/41916 | 11/1997 |
| WO | 97/43961 | 11/1997 |
| WO | 98/02099 | 1/1998 |
| WO | WO 98/03118 | 1/1998 |
| WO | 98/06356 | 2/1998 |
| WO | 98/08456 | 3/1998 |
| WO | 98/10714 | 3/1998 |
| WO | 98/16161 | 4/1998 |
| WO | 98/19607 | 5/1998 |
| WO | 98/19625 | 5/1998 |
| WO | WO 98/38939 | 9/1998 |
| WO | WO 98/38941 | 9/1998 |
| WO | WO 98/38942 | 9/1998 |
| WO | 98/44869 | 10/1998 |
| WO | 98/46115 | 10/1998 |
| WO | 98/46119 | 10/1998 |
| WO | 98/49964 | 11/1998 |
| WO | 98/54759 | 12/1998 |
| WO | 98/55027 | 12/1998 |
| WO | WO 98/57590 | 12/1998 |
| WO | 98/57591 | 12/1998 |
| WO | WO 98/57592 | 12/1998 |
| WO | WO 99/08603 | 2/1999 |
| WO | 99/08624 | 2/1999 |
| WO | 99/49793 | 3/1999 |
| WO | 99/17683 | 4/1999 |
| WO | 99/21490 | 5/1999 |
| WO | 99/21510 | 5/1999 |
| WO | 99/22656 | 5/1999 |
| WO | 99/25273 | 5/1999 |
| WO | 99/32051 | 7/1999 |
| WO | WO 99/35979 | 7/1999 |
| WO | 99/36000 | 7/1999 |
| WO | 99/36001 | 7/1999 |
| WO | 99/37218 | 7/1999 |
| WO | 99/38459 | 8/1999 |
| WO | 99/40868 | 8/1999 |
| WO | 99/47071 | 9/1999 |
| WO | 99/47078 | 9/1999 |
| WO | 99/48427 | 9/1999 |
| WO | 99/48545 | 9/1999 |
| WO | 99/49910 | 10/1999 |
| WO | 99/51162 | 10/1999 |
| WO | WO 99/52475 | 10/1999 |
| WO | 99/53863 | 10/1999 |
| WO | 99/60941 | 12/1999 |
| WO | 99/62439 | 12/1999 |
| WO | 00/09195 | 2/2000 |
| WO | 00/10623 | 3/2000 |
| WO | 00/12029 | 3/2000 |
| WO | 00/15146 | 3/2000 |
| WO | 00/15147 | 3/2000 |
| WO | 00/15148 | 3/2000 |
| WO | 00/15149 | 3/2000 |
| WO | 0015275 | 3/2000 |
| WO | 00/18325 | 4/2000 |

| | | |
|---|---|---|
| WO | 00/18326 | 4/2000 |
| WO | 00/18331 | 4/2000 |
| WO | 00/21436 | 4/2000 |
| WO | 00/21461 | 4/2000 |
| WO | 00/21463 | 4/2000 |
| WO | 00/24449 | 5/2000 |
| WO | 00/33725 | 6/2000 |
| WO | 00/35376 | 6/2000 |
| WO | WO 00/36997 | 6/2000 |
| WO | 00/41632 | 7/2000 |
| WO | 00/41633 | 7/2000 |
| WO | 00/45711 | 8/2000 |
| WO | WO 00/45886 | 8/2000 |
| WO | 00/56387 | 9/2000 |
| WO | 00/66007 | 11/2000 |
| WO | 00/66009 | 11/2000 |
| WO | 00/66035 | 11/2000 |
| WO | 00/71195 | 11/2000 |
| WO | 01/08602 | 2/2001 |
| WO | 01/10340 | 2/2001 |
| WO | 01/10341 | 2/2001 |
| WO | 01/10347 | 2/2001 |
| WO | 01/10348 | 2/2001 |
| WO | 01/10349 | 2/2001 |
| WO | WO 01/10350 A1 | 2/2001 |
| WO | 01/17440 | 3/2001 |
| WO | 01/17456 | 3/2001 |
| WO | 01/26562 | 4/2001 |
| WO | 01/49187 | 7/2001 |
| WO | 01/54625 | 8/2001 |
| WO | 01/60427 | 8/2001 |
| WO | 01/70133 | 9/2001 |
| WO | 01/78801 | 10/2001 |
| WO | 01/82803 | 11/2001 |
| WO | 01/82837 | 11/2001 |

OTHER PUBLICATIONS

Gardner M.D. et al., "An Experimental Anatomic Study of Indirect Myocardial Revascularization," *Journal of Surgical Research*, May 1971, vol. 11, No. 5, pp. 243–247.

Palmaz et al., "Expandable Intrahepatic Portacaval Shunt Stents: Early Experience in the Dog," *AJR*, 1985, vol. 145, pp. 821–825.

Palmaz et al., "Expandable Intrahepatic Portacaval Stunt Stents in Dogs with Chronic Portal Hypertension," *AJR*, 1988, vol. 147, pp. 1251–1254.

Richter, M.D. et al., "Transjugular Intrahepatic Portacaval Stent Shunt: Preliminary Clinical Results," *Radiology*, 1990, vol. 174, No. 3, pp. 1027–1030.

Zemel, M.D. et al., "Percutaneous Transjugular Portosystemic Shunt," *JAMA*, 1991, vol. 266, No. 3, pp. 390–393.

Massimo, M.D. et al., "Myocardial Revascularization by a New Method of Carrying Blood Directly from the Left Ventricular Cavity into the Coronary Circulation," *Journal of Thoracic Surgeons*, Aug. 1997, vol. 34, No. 2, pp. 257–264.

Lary, M.D. et al., "Myocardial Revascularization Experiments Using the Epicardium," *Archives of Surgery*, Jan. 1969, vol. 98, No. 1, pp. 69–72.

Munro, M.D. et al., "The possibility of myocardial revascularization by creation of a left ventriculocoronary artery fistula," *Journal of Thoracic and Cardiovascular Surgery*, Jul. 1969, vol. 58, No. 1, pp. 25–32.

Kuzela, M.D. et al., "Experimental evaluation fo direct transventricular revascularization," *The Journal of Thoracic and Cardiovascular Surgery*, Jun. 1969, vol. 57, No. 6, pp. 770–773.

Levinsky, L. et al., "The Revival of the Horseshoe Graft," *Thorac.cardiovasc. Surgeon*, 27, pp. 322–324, 1979.

Mills, Noel L. et al., "Valvulotomy of valves in the saphenous vein graft before coronary artery bypass," *The Journal of Thoracic and Cardiovascular Surgery*, 71(6), pp. 878–879, Jun. 1976.

Baba et al., "Hemodynamic effects of venous valves in aorto–coronary bypass grafts," *The Journal of Thoracic and Cardiovascular Surgery*, 71(5), pp. 774–778, May 1976.

Phillips, Steven J. M.D. et al, "Improvement in Forward Coronary Blood Flow by Using a Reversed Saphenous Vein with a Competent Valve," *The Annals of Thoracic Surgery*, 21(1), pp. 12–15, Jan. 1976.

Tweden et al., "Ventriculocoronary Artery Bypass (VCAB), a Novel Approach to Myocardial Revascularization," #2000–4653, Feb. 2000.

* cited by examiner

A-B-C-D-G-H-A : CORONARY ARTERY
G-D-E-F-G : SHUNT FROM LEFT VENTRICLE
A-H : WALL BOUNDARY
A-B,C-D-E, F-G-H : WALL BOUNDARY
E-F : PRESSURE BOUNDARY CONDITION
B-C : PRESSURE BOUNDARY CONDITION

| CONFIGURATION | R "TO VENTRICLE" /R "TO ARTERY" @ 100 ml/min | R "TO VENTRICLE" /R "TO ARTERY" @ 200 ml/min | RELATIVE RESISTANCE @ 100 ml/min FUNNEL = 1 |
|---|---|---|---|
| CONSTANT I.D., 90 DEG ENTRY | 0 | SLIGHT | 3 |
| CONSTANT ID, 30 DEG ENTRY | 1.2 | 1.38 | 2 |
| FUNNEL, STENT ONLY | 0 | 0 | 1 |
| FUNNEL, 90 DEG ENTRY | 0 | 1.2 | 2.5 |
| KAMM .052 THROAT DIA., 90 DEG. ENTRY | 1.2 | 1.25 | 7.8 |
| KAMM .040 THROAT DIA., 30 DEG. ENTRY | 1.3 | 1.25 (@ 150 ml/min* | 20 |
| KAMM .052 THROAT DIA., STENT ONLY | 1.4 | 1.6 | 5.3 |

FIG. 19

CONDUIT DESIGNS AND RELATED METHODS FOR OPTIMAL FLOW CONTROL

CROSS REFERENCE TO RELATED APPLICATIONS

This application claims the benefits of priority of provisional application Serial No. 60/153,205, filed Sep. 10, 1999, the entire disclosure of which is hereby incorporated by reference herein.

FIELD OF THE INVENTION

This invention relates to an apparatus and method for implanting a conduit to allow communication of fluids from one portion of a patient's body to another. The invention more particularly relates to a blood flow conduit implanted in a heart to allow direct flow communication between a heart chamber and a vessel and/or between two vessels. Even more particularly, the invention relates to left ventricular conduit designs and configurations, and methods for optimizing conduit designs, for controlling the flow of blood through the conduit to achieve a direct bypass of an occluded coronary artery and for optimizing total blood flow through coronary arteries with variations in proximal occlusions.

BACKGROUND OF THE INVENTION

Coronary artery disease is a major problem in the U.S. and throughout the world. In fact, about 1.1 million "open heart" procedures are performed each year, and current estimates are that approximately 4.8 million people suffer from some degree of congestive heart failure.

When coronary arteries or other blood vessels become clogged with plaque, the results are at the very least impairment of the efficiency of the heart's pumping action. More severe results include heart attack and/or death. In some cases, clogged arteries can be unblocked through minimally invasive techniques such as balloon angioplasty. In more difficult cases, a surgical bypass of the blocked vessel is necessary.

In a bypass operation, one or more arterial or venous segments are harvested from the body and then surgically inserted between the aorta and the coronary artery. The inserted vessel segments, or transplants, act as a bypass of the blocked portion of the coronary artery and thus provide for a free or unobstructed flow of blood to the heart. More than 500,000 bypass procedures are performed in the U.S. every year.

Coronary artery bypass grafting (CABG) has been used for more than 30 years. Initially, the saphenous vein (SV) served as the principal conduit for coronary bypass, but studies over the last dozen years have shown a 35–40% increase in 10-year patency rate or the internal thoracic artery (ITA) compared with SV. The SV, in fact, has only been shown to have a 10-year patency rate of 50%. Since the mid 1980's, not only the ITA, but also the alternative arterial conduits have been increasingly used. These conduits include the gastroepiploic artery (GEA), inferior epigastric artery (IEA), and radial artery (RA), which have been used primarily as supplements to both the right and left ITA.

Although the use of arterial conduits results in demonstrably better long-term patency, use of arteries in place of the SV often requires complex technical challenges, such as free grafts, sequential anastomosis, and conduit-to-conduit-anastomosis. Some of the reasons for the difficulty in using arterial conduits reside in the fact that they are much more fragile than the SV and therefore easier to damage, and due to their smaller size, easier to occlude completely or partially through technical error during grafting.

Such coronary artery bypass surgery, however, is a very intrusive procedure that is expensive, time-consuming and traumatic to the patient. The operation requires an incision through the patient's sternum (sternotomy), and the patient being placed on a bypass pump so that the heart can be operated on while not beating. A vein graft is harvested from the patient's leg, another highly invasive procedure, and a delicate surgical procedure is required to piece the bypass graft to the coronary artery (anastomosis). Hospital stays subsequent to the surgery and convalescence periods are prolonged.

As mentioned above, another conventional treatment is percutaneous transluminal coronary angioplasty (PTCA) or other types of angioplasty. However, such vascular treatments are not always indicated due to the type or location of the blockage, or due to the risk of the emboli formation.

One bypass technique employs a stent introduced through the myocardial wall from an adjacent coronary artery to provide a direct bypass conduit between the left ventricle and the adjacent coronary artery. In one embodiment, this technique includes the delivery of a transmyocardial bypass shunt in a collapsed, reduced-profile configuration, which requires radial expansion subsequent to delivery in a bore pre-formed in the myocardial wall. The stent may extend completely through the myocardium to establish a blood flow path or conduit directly from the left ventricle to a coronary artery; downstream of a vascular obstruction or occlusion in a proximal part of the artery.

The configurations of these direct bypass conduits, which can be in the form of stents or shunts, or other similar devices, have had promising results in performing as a direct blood flow path from the left ventricle to the coronary artery. However, there is a continuing need for improved bypass methods and conduits configured to control and optimize coronary blood flow, especially to prevent or hinder loss of blood in the artery due to backflow during diastole, and for conduits that are more precisely adapted to the level of arterial occlusion experienced by a particular patient.

SUMMARY OF THE INVENTION

The advantages and purpose of the invention will be set forth in part in the description which follows, and in part will be obvious from the description, or may be learned by practice of the invention. The advantages and purpose of the invention will be realized and attained by means of the elements and combinations particularly pointed out in the appended claims.

An aspect of the present invention includes a bypass conduit for implantation in a heart to bypass an at least partially occluded artery. The bypass conduit includes a first end defining a first opening and a second end opposite the first end defining a second opening. A wall extends between the first and second ends and defines a lumen extending between the first and second openings. The ends and the wall of the conduit are configured such that the conduit has a greater resistance to blood flow in a first direction than in a second direction.

Another aspect of the present invention includes a bypass conduit for implantation in a heart to bypass an at least partially occluded artery. The bypass conduit includes a first end defining a first opening and a second end opposite the first end defining a second opening. A wall extends between the first and second ends and defines a lumen extending between the first and second openings. The conduit is configured to have a greater resistance to blood flow in a first direction than in a second direction without any active flow control mechanism.

Yet another aspect of the invention includes a method of bypassing an at least partially occluded artery, comprising determining a resistance to blood flow of the artery at a location of an at least partial occlusion and selecting a conduit having a configuration based on the resistance to flow of the artery at the location of the at least partial occlusion. The method further comprises implanting the conduit in a heart wall between a heart chamber and the artery downstream of the at least partial occlusion to directly flow blood between the chamber and the artery.

BRIEF DESCRIPTION OF THE DRAWINGS

The accompanying drawings, which are incorporated in and constitute a part of this specification, illustrate embodiments of the invention and together with the description, serve to explain the principles of the invention.

FIG. 15a is a vector velocity plot of the fluid dynamic analysis performed for the conduit shown in FIG. 14a;

FIG. 18a is a graph of experimental results of flow versus pressure corresponding to experiments using the conduit of FIG. 16a;

FIG. 19 is a table containing various experimental results of flow resistance ratios for the conduits and setups of FIGS. 16a–16c and 17a–17c, respectively;

DETAILED DESCRIPTION OF THE INVENTION

Figure 1:
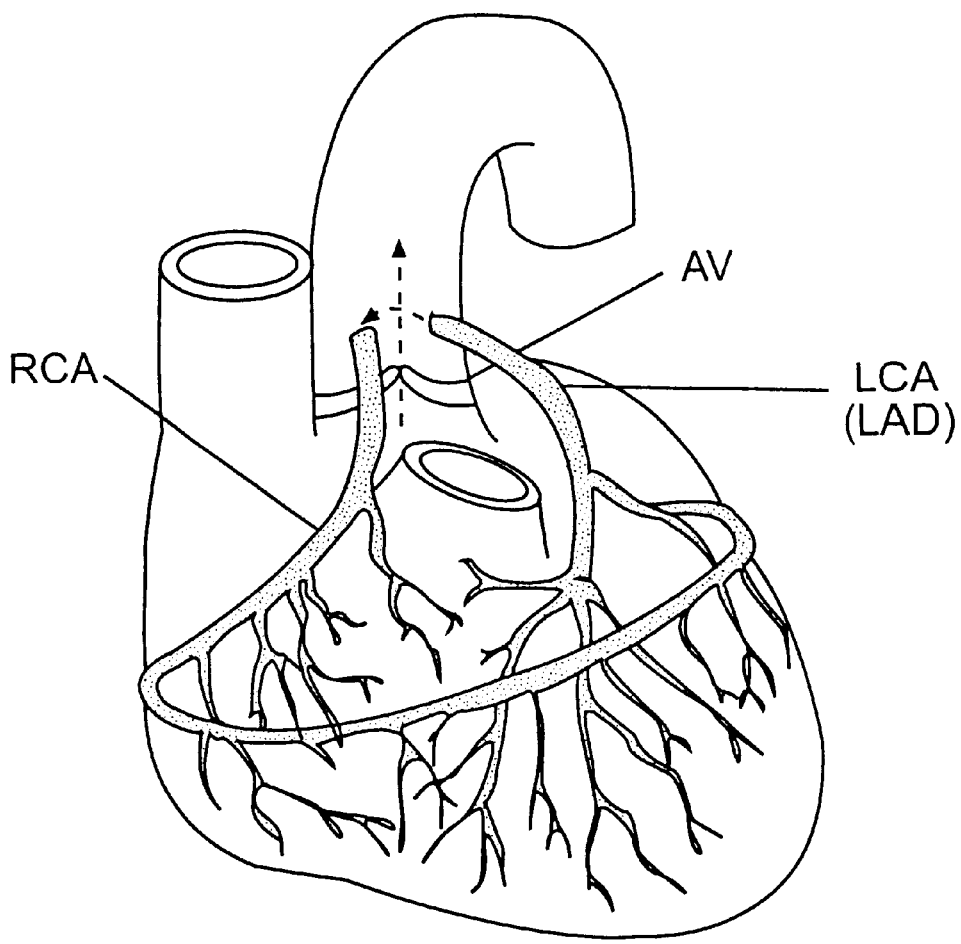
FIG. 1 is a schematic view of a heart showing the left and right coronary artery circulation.

Through various aspects of the present invention, it has been determined that for some levels of coronary occlusion, a conduit having an asymmetrical flow resistance may be necessary in order to provide a beneficial blood flow through the artery. As used herein, an asymmetrical flow resistance means that the resistance to flow through the conduit in one direction is different than the resistance to flow through the conduit in the opposite direction, and symmetrical flow resistance means that the resistance to flow through the conduit is the same in both directions. In the cases where a coronary artery is completely occluded, it has been found that a conduit having a symmetrical flow resistance produces an increase in mean blood flow through the coronary artery. The blood flow through the coronary artery decreases as the symmetrical flow resistance increases. On the other hand, in certain cases where the coronary artery is not totally occluded, as will be explained, a conduit having a symmetrical flow resistance may not improve the amount of blood flow through the coronary artery that is already able to pass through the partial occlusion, and thus will provide no benefit to a patient. Although conduits that resist flow more strongly in the direction from the coronary artery to the left ventricle are desirable for any level of arterial stenosis, including totally occluded, in certain cases of partial occlusions, it is preferred that the implanted conduit have a high enough asymmetrical flow resistance in order to transition from a non-beneficial situation (i.e., the implanted conduit results in less total coronary flow than would be experienced without the conduit) to a beneficial one (i.e., the implanted conduit increases total coronary flow to more than it would be without a conduit). In other words, a conduit that allows or more easily permits forward systolic flow from the left ventricle to the artery but prevents or hinders diastolic backflow from the artery to the ventricle is desired, and in certain cases of stenosed arteries there exists a preferred, threshold target ratio of resistance of diastolic backflow to the resistance of systolic forward flow in order to achieve beneficial results in total coronary flow when the direct bypass conduit is implanted in the heart.

Furthermore, it is desirable to provide such a conduit having an asymmetrical flow resistance without the use of valves or other mechanical or moving parts due to the small dimensions of the conduits and corresponding valve and other mechanical flow control mechanisms. Such active movable or other articulating devices may be complicated and/or expensive to manufacture, particularly on the small scales required in contexts such as passing blood directly from the left ventricle to the coronary artery, for example. Also, an increased risk of thrombosis may result from irregular surfaces associated with such valves and other mechanical flow control mechanisms. Thus, in designing conduits to optimize fluid or blood flow through them, the design or configuration of conduits according to the invention preferably is such that the conduit automatically, or passively, achieves flow control without microvalves, check valves, or other active or movable devices and parts. Such passive flow control devices can be designed into the geometry, configuration, or other characteristics, including implantation geometry and the like, of the conduit such that flow is biased in one direction. Thus, flow within and/or completely through the conduit may occur in either direction (whether simultaneously or severally), but net or mean flow in the desired direction can be maximized by maximizing flow in that direction and/or minimizing flow in the opposite direction. Passive flow control devices may comprise various conduit configurations, as will be explained in more detail with reference to FIGS. 16a and 20–26, such as, for example, tapers in the lumen or a changing inner diameter of the conduit, tapers and/or radii of curvature at the openings of the conduit, the angle of insertion of the conduit with respect to the axis of the coronary artery, and other similar conduit design characteristics or implantation characteristics.

Thus, in certain embodiments according to the present invention, flow control is achieved by maximizing flow through the conduit in one direction, preferably from the left ventricle to the coronary artery, and minimizing flow through the conduit in the opposite direction, preferably from the coronary artery to the left ventricle. Since the flow rate is a function of friction, drag, turbulence, and other fluid dynamic parameters, it is convenient for the purposes of this application to discuss flow rate through the conduit in terms of resistance of the conduit to such flow. In other words, in certain embodiments of the bypass conduits according to the present invention, it is preferred to have a low conduit resistance in the forward direction from the left ventricle to the coronary artery (also called the systolic flow resistance), and a higher resistance in the backward direction from the coronary artery to the left ventricle (also called the diastolic flow resistance).

As mentioned above and explained in more detail shortly, computer simulation and experimentation has shown that the characteristics producing optimized flow rate in the coronary artery may depend on the degree of occlusion in the artery. Thus, preferably the conduit design or implantation configuration should be selected in each case such that flow rate through the conduit is controlled to enhance total coronary flow, thereby enhancing perfusion of the heart tissues. It has been determined that, where a proximal occlusion is only partial, the total flow rate in the distal coronary artery may or may not be increased by the placement of a conduit. If the conduit resistance is symmetric, i.e., the same in both the forward and backward directions, total flow may actually decrease when a bypass conduit is implanted in the heart wall due to a relatively high diastolic backflow through the conduit from the coronary artery to the left ventricle. In such cases, a patient may not benefit from placement of the bypass conduit. If the conduit resistance is asymmetrical, however, such that diastolic flow resistance is higher than systolic flow resistance, the total distal coronary flow may in such cases. The increase in total flow may be large enough such that for levels of occlusion for which placement of a conduit having symmetrical resistance are detrimental, the placement of a conduit having an asymmetrical flow resistance may produce a benefit to the patient due to an overall increase in total coronary flow. Moreover, computer simulations have shown that conduits designed to have an asymmetrical flow resistance ratio of backward resistance to forward resistance of approximately 2 produce beneficial results in flow through certain degrees of partially occluded arteries. Experimental results have shown that conduits can be designed to passively achieve asymmetrical flow resistance ratios near a value of 2.

Computer Simulation

An aspect of the present invention relates to a computer model designed to simulate the physiological system dynamics of the cardiovascular system, including simulating the system dynamics of a cardiovascular system in which a coronary bypass conduit with various characteristics has been implanted in the heart wall to directly flow blood from the left ventricle to the coronary artery. The computer model can thus be used to predict the hemodynamic effects of a bypass using various types of conduits having different characteristics according to the invention. Moreover, as will be explained, by performing parametric studies utilizing the computer model, it has been determined that modifying conduit designs and characteristics depending on the degree of occlusion of the artery optimizes blood flow through the coronary artery.

FIG. 1 shows a schematic of a heart H with blood flowing up through the aortic valve AV (as indicated by the arrow) into the right coronary artery RCA and the left coronary artery LCA. As shown in FIG. 1, the blood travels into various branches of the coronary arteries and ultimately feeds the heart wall muscle. Thus, when an artery becomes occluded, blood is prevented or hindered from flowing through the artery to the heart wall muscle, which receives almost its entire nutritive blood supply from the arteries.

Figure 2:
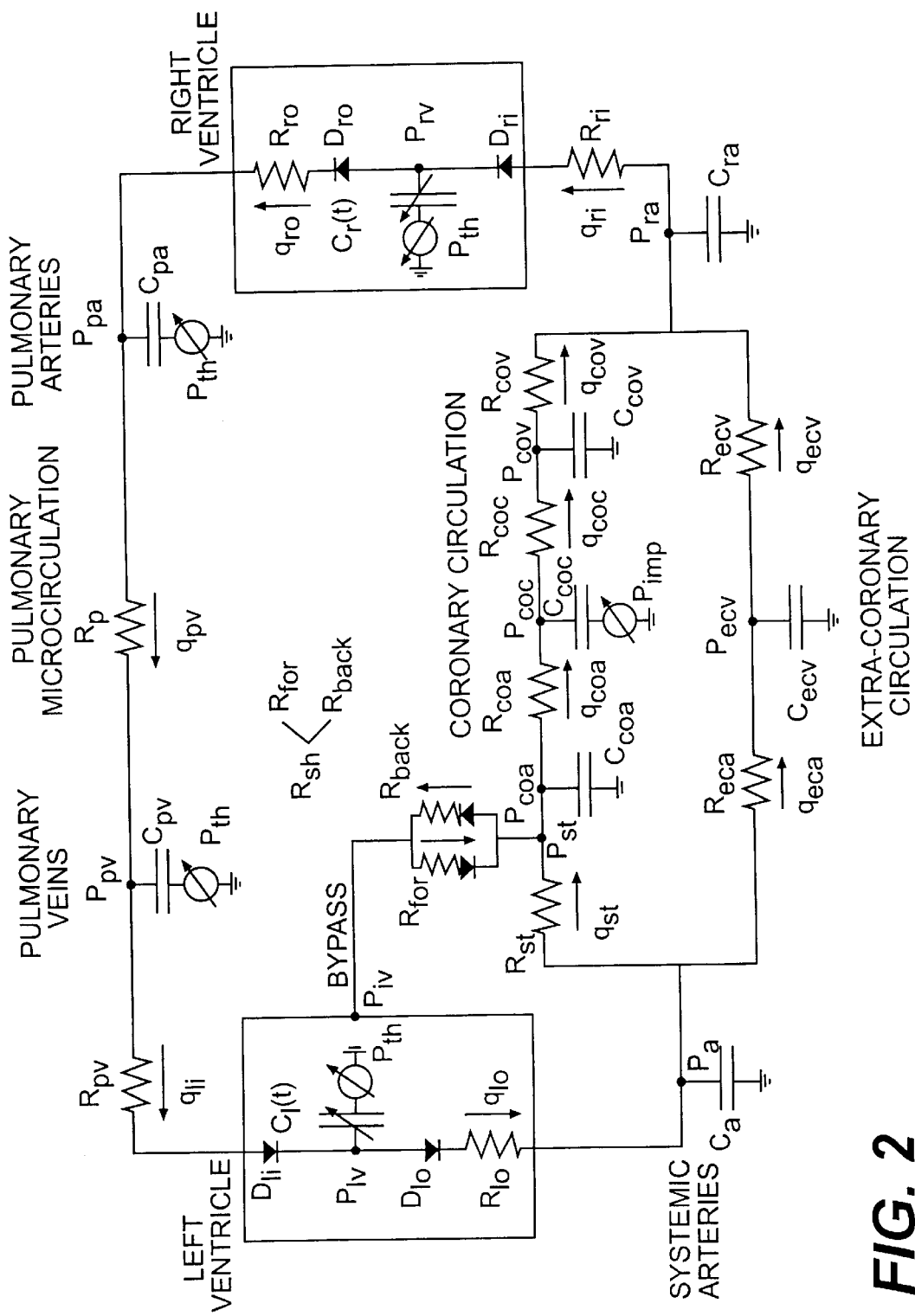
FIG. 2 is a schematic diagram of the lumped parameter model computer code, with emphasis on the coronary circulation, according to an aspect of the present invention.

As shown in FIG. 2, the computer code of the present invention is based on a lumped parameter model of the total cardiovascular circulation, with emphasis on the coronary circulation. Essentially, the model according to the invention inserts the coronary circulation and bypass circulation into an existing model of the cardiovascular system, previously developed by Davis. See Davis, T. D. "Teaching physiology through interactive simulation of hemodynamics," *MIT M.S. Thesis*, Cambridge, Mass. 1991, the complete disclosure of which is incorporated herein by reference. The existing model includes arterial, venous, and pulmonary circulations and simulates autoregulation functions such as the baroreceptor reflex for short term control of blood pressure and the cardiopulmonary reflex for control of blood volume. One reason for implementing the coronary circulation in a complete cardiovascular (CV) model is that the baroreflex and cardiopulmonary reflex can be utilized to examine a variety of realistic conditions that might be experienced by patients after coronary bypass surgery. In addition, it permits the study of how the surgically altered system will perform in conjunction with the rest of the circulation.

Kirchoff's Equation is applied to each of the nodes of the lumped parameter model shown in FIG. 2, which yields a matrix equation in the form:

$$dp/dt=Ap+b$$

where p represents the vector of compartmental pressures, A represents the time constants for exchange between compartments, and b is the input to the system. Detailed expressions of the model equations and the meaning of the various expressions used in these equations can be found in Appendix A. From the description of the computer model herein, including the model shown in FIG. 2, the expressions of the computational procedure of Appendix A, and their corresponding written descriptions, one skilled in the art of computer modeling and/or programming can devise the appropriate software and/or code to perform the computer simulation according to the present invention.

In FIG. 2, diodes are used to ensure unidirectional flow. Each compartment, or volume adapted to contain or flow blood, is characterized by an inflow resistance $R_i$ measured in peripheral resistance units (PRU) with a unit of mmHg-s/ml, a compliance C, which is the change in volume associated with a given change in pressure and essentially is a measure of the flexibility of the compartment, with a unit of ml/mmHg, a volume at zero transmural pressure $V_0$ (zero pressure filling volume, ZPFV) with a unit of ml, and an outflow resistance $R_0$, again measured in PRU. Transmural pressure across the pulmonary capacitance varies according to intra-thoracic pressure. As can be seen, the model also includes different flow resistance values, $R_{for}$ and $R_{back}$, according to flow direction for the conduit or shunt. Actually, even for an implanted conduit in the form of a straight tube with a constant inner diameter (i.e., a symmetrical resistance conduit), the resistance in case of forward direction (from the left ventricle to the coronary artery) and the backward direction (from the coronary artery to the left ventricle) may not be exactly equal. However, the forward and backward resistances are assumed to be equal in the case of such a symmetrical resistance conduit for the purposes of the experiments and studies presented herein. The various parameter values for each node, along with the source from which some of the values were determined, can be found in Appendix B. "Davis, 1991" refers to Davis, T. D., "Teaching physiology through interactive simulation of hemodynamics," *MIT M.S. Thesis*, Cambridge, Mass. 1991. "Ursino, 1998" refers to Ursino, M., "Interaction between carotid baroregulation and the pulsating heart: a mathematical model," *Am. J. Physiol.*, 275, H1733–H1747, 1998. "Schreiner, 1989" refers to Schreiner, W., et al., "Simulation of coronary circulation with special regard to the venous bed and coronary sinus occlusion," *J. Biomed. Eng.*, 12, 429–443.

Figure 3:
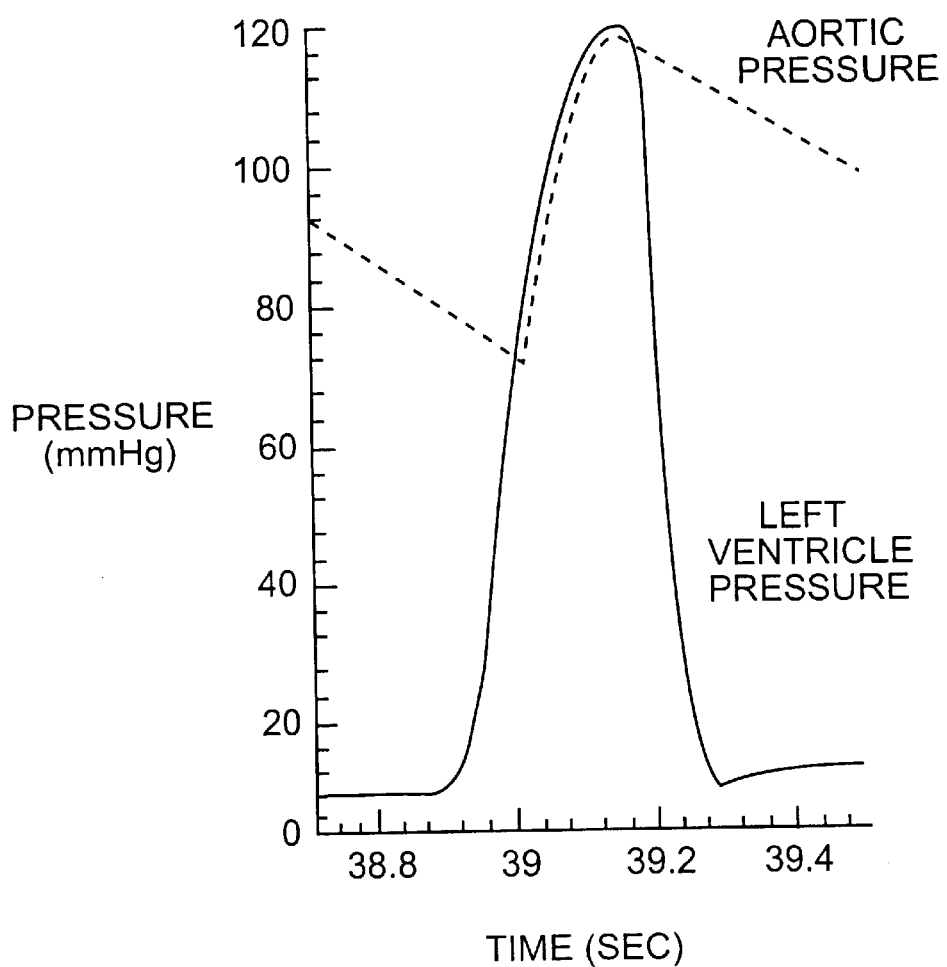
FIG. 3 is a graph of the left ventricular and aortic pressures through one cardiac cycle, as computed by the model.

Because the blood flow through the coronary circulation is relatively small in comparison to the total circulation of blood through the system, the coronary circulation has a relatively minor effect on the overall circulation. In contrast, the aortic and left ventricular pressures determined from the overall circulation become one of the main inputs into the coronary circulation portion of the model. FIG. 3 illustrates the left ventricular and aortic pressures through one cardialc cycle, as computed by the model. The portion of the left ventricle pressure forming the peak (from about 39 seconds to 39.2 seconds in the figure) corresponds essentially to systole.

Figures 4A, 4B:
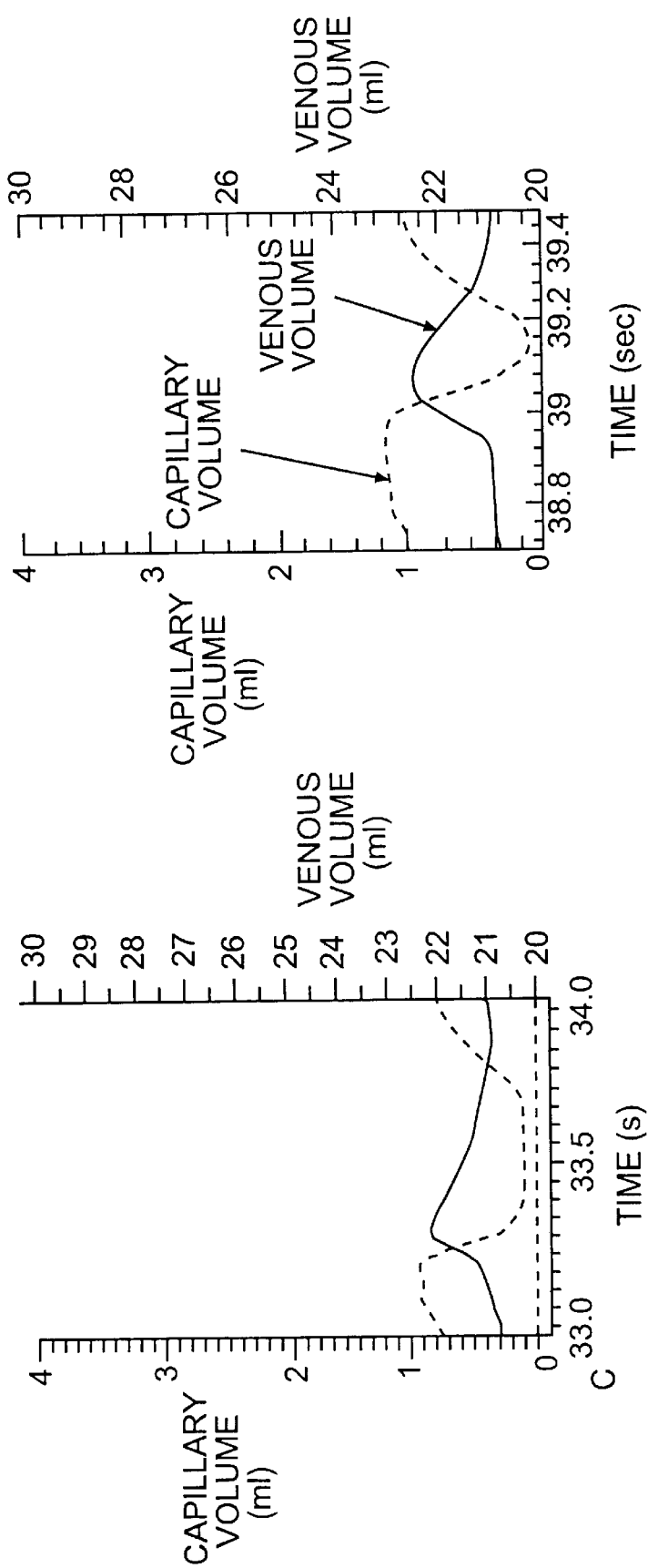
FIG. 4a is a graph of capillary volume (dotted line) and venous volume (solid line) versus time, as obtained from the lumped parameter model of FIG. 2 according to an aspect of the invention.
FIG. 4b is a graph of capillary volume (dotted line) and venous volume (solid line) versus time obtained from previous computations.

FIGS. 4a–6b show a comparison of results obtained from the lumped parameter model with results obtained from previous computations and experiments. FIG. 4a is a graph of capillary volume (dotted line) and venous volume (solid line) versus time, as obtained from the lumped parameter model, and FIG. 4b is a graph of capillary volume (dotted line) and venous volume (solid line) versus time obtained from previous computations. FIG. 5a is a graph of the flow to capillaries (dotted line) and the flow to veins (solid line) versus time, as obtained from the lumped parameter model, and FIG. 5b is a graph of the flow to capillaries (dotted line) and the flow to veins (solid line) versus time, as obtained from previous computations. The results shown in the graphs corresponding to the previous computations were obtained from Schreiner, W. et al., "Simulation of coronary circulation with special regard to the venous bed and coronary sinus occlusion," *J. Biomed. Eng.*, 12, pp. 429–43 (1990). The time periods shown in these figures correspond to the cardiac cycle period shown in FIG. 3. Moreover, the results shown in FIGS. 4a–5b correspond to the simulation and computation of coronary circulation in a normal state, that is, without occlusions and without a bypass conduit directly inserted in the heart wall ($R_{st}=0$ and $R_{sh}=\infty$). Thus, these results serve as a verification of the computer model when used for modeling the flow in a normal state.

Figures 5A, 5B:
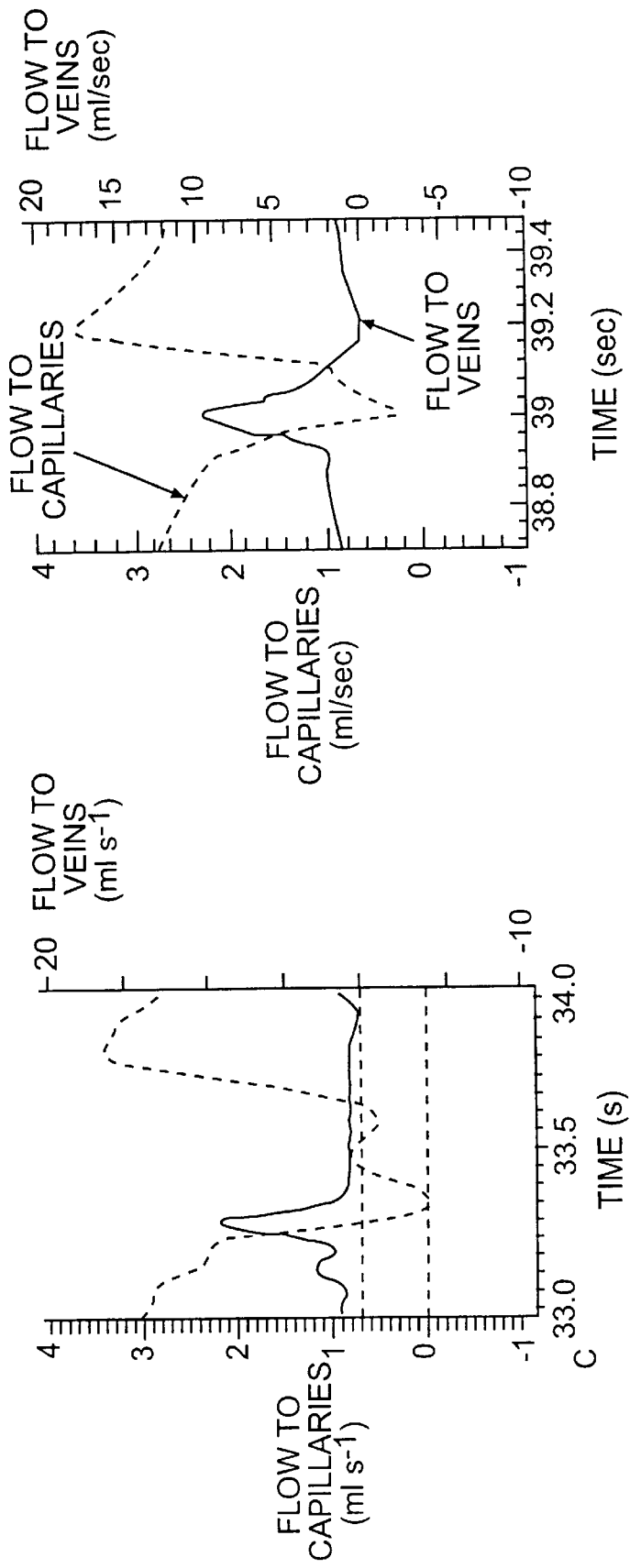
FIG. 5a is a graph of the flow to capillaries (dotted line) and the flow to veins (solid line) versus time, as obtained from the lumped parameter model of FIG. 2 according to an aspect of the invention.
FIG. 5b is a graph of the flow to capillaries (dotted line) and the flow to veins (solid line) versus time, as obtained from previous computations.

As can be seen in FIGS. 5a and 5b, during systole the flow rate to the coronary capillaries decreases due to the increased resistance resulting from the contraction of myocardial muscle, whereas flow through the coronary veins increases due to compression of the capillaries and small veins. The change of capillary and venous volume, as shown in FIGS. 4a and 4b, varies in a manner similar to the flow rate variations shown in FIGS. 5a and 5b. In the present simulations, however, peak systolic pressure is not sustained for as long a time period as in the previous computations. This results in a relatively narrower band of reduced capillary flow rate, as shown in FIG. 5b.

To further verify the computer model, the coronary flow and conduit, or shunt, flow were simulated for a human having a totally occluded left anterior descending coronary artery with a bypass conduit implanted in the heart wall to directly flow blood from the left ventricle to the coronary artery. The bypass conduit modeled was a constant diameter tube having a symmetrical flow resistance of 1.147 PRU. The simulated results were compared to experimental results in a dog with a totally occluded artery and a bypass conduit having a symmetrical flow resistance of approximately 1.147 PRU implanted in the heart and configured to directly flow blood from the left ventricle to the artery.

Figure 6A:
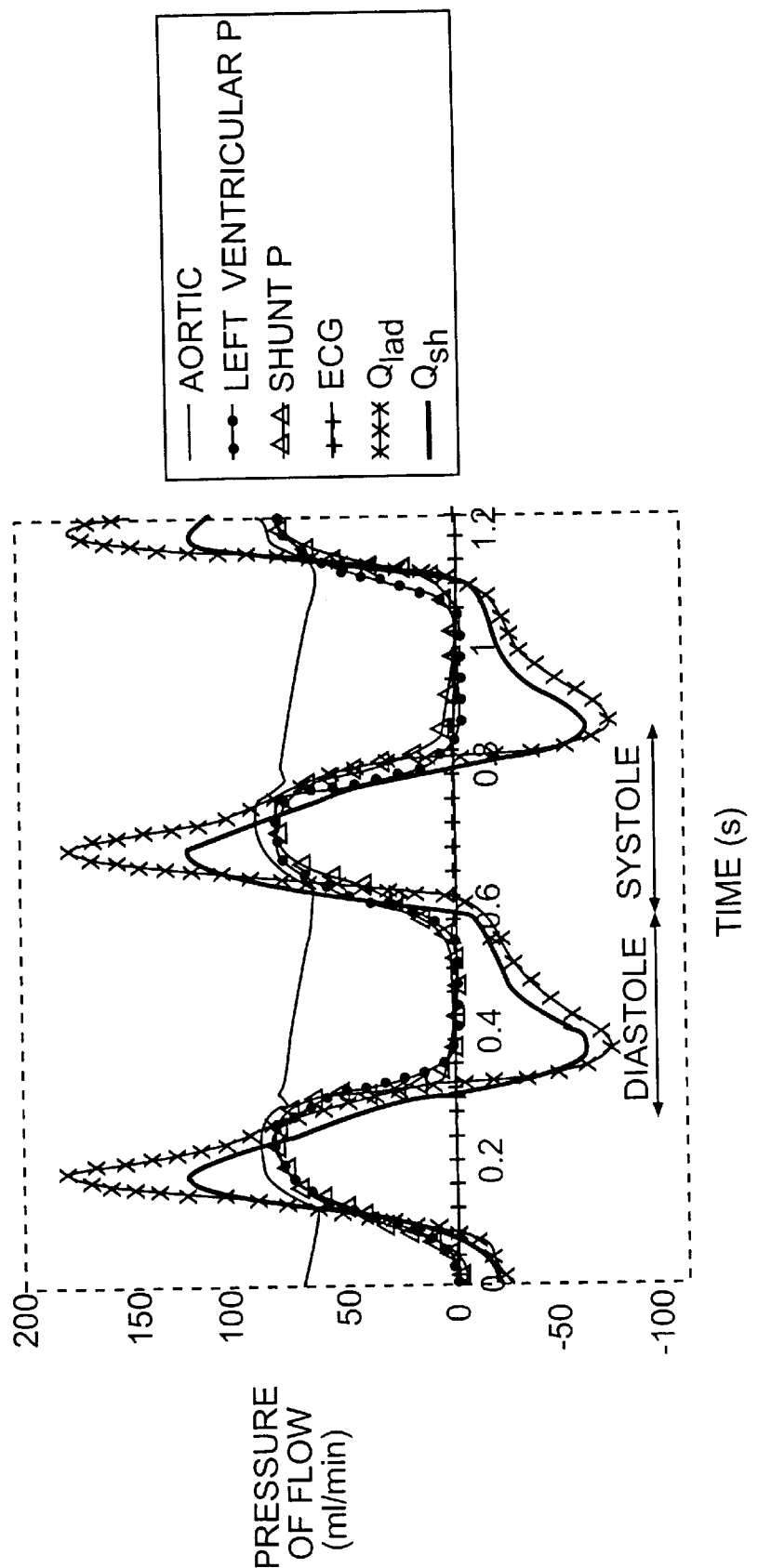
FIG. 6a is a graph of various hemodynamic parameters obtained from experiments performed in a dog with an occluded artery and a bypass conduit implanted in the heart wall to directly flow blood from the left ventricle to the artery.

FIG. 6a is a graph of various hemodynamic parameters obtained from experiments performed in a dog with a totally occluded coronary artery and a bypass conduit in the form of a tube of constant inner diameter with a symmetrical flow resistance implanted in the heart wall at an entry angle in the coronary artery of 90° and configured to directly flow blood from the left ventricle to the coronary artery The flow rate through the shunt is represented by the line corresponding to $Q_{sh}$ and the flow rate through the occluded coronary artery is represented by the line corresponding to $Q_{lad}$.

Figure 6B:
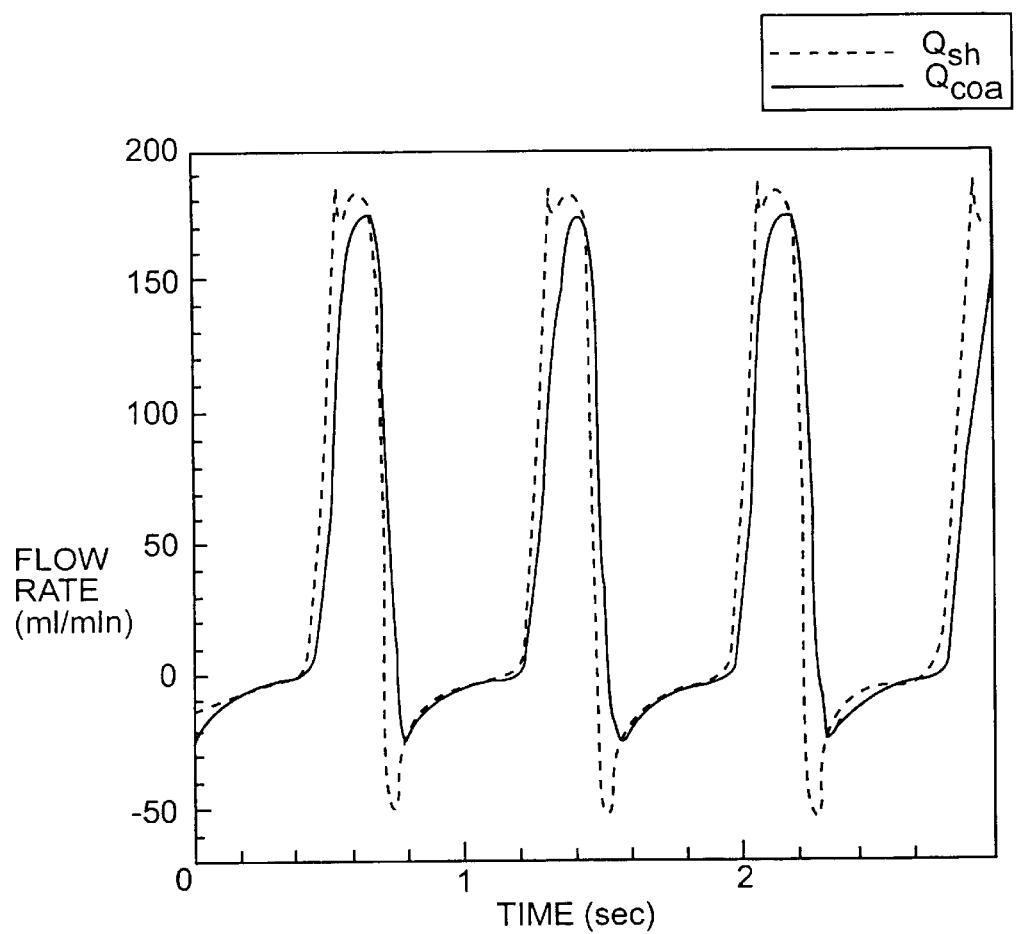
FIG. 6b is a graph showing the results obtained using the computer program to model the coronary circulation in a human having a totally occluded coronary artery with a bypass conduit implanted in the heart wall to directly flow blood from the left ventricle to the artery.

FIG. 6b is a graph showing the results obtained using the computer program to model the coronary circulation in a human having a totally occluded coronary artery with a bypass conduit having a symmetrical flow resistance (i.e., simulating the constant diameter conduit used in the experiments) implanted in the heart wall to directly flow blood from the left ventricle to the coronary artery, as described above. To model a totally occluded artery, the value of $R_{st}$ is set to infinity. The results shown in FIG. 6b are the flow rate through the shunt ($Q_{sh}$) and the flow rate through the artery ($Q_{lad}$). As can be seen in both the results obtained from experiment and from the computer simulation, a large back flow, shown by the negative flow rate through the coronary artery and a negative flow rate through the shunt, occurs during diastole due to the corresponding decreased pressure in the left ventricle.

After verifying the accuracy of the computer model, as shown in FIGS. 4a–6b, the it model was used to perform a series of parametric studies simulating the effects on the coronary circulation of bypass procedures by varying conduit characteristics and level of occlusion in the coronary artery. A portion of the parametric study focused on assuming a conduit or shunt resistance $R_{sh}$ independent of the direction of flow through the conduit, i.e., a symmetrical resistance. The Poiseuille flow assumption was used to first obtain a reference value of the conduit, or shunt, resistance for a conduit having a diameter of 2 mm and a length of 2 cm. Under this assumption, the flow rate in the conduit is given by the following expression:

$$Q = \frac{\pi D^4 \Delta P}{128 \mu L} = \frac{\Delta P}{R_{sh}}$$

where Q is the flow rate in the conduit, and D, ΔP, and t represent diameter, pressure drop through the conduit length, and fluid viscosity, respectively. From the relation above, the expression for the conduit, or shunt, resistance thus becomes $$R_{sh} = \frac{128 \mu L}{\pi D^4}$$

Using the length and diameter of a typical shunt discussed above and a fluid viscosity of 0.03 kg/m-s, which represents blood, the calculated conduit resistance is approximately 1.147 PRU.

Figure 7:
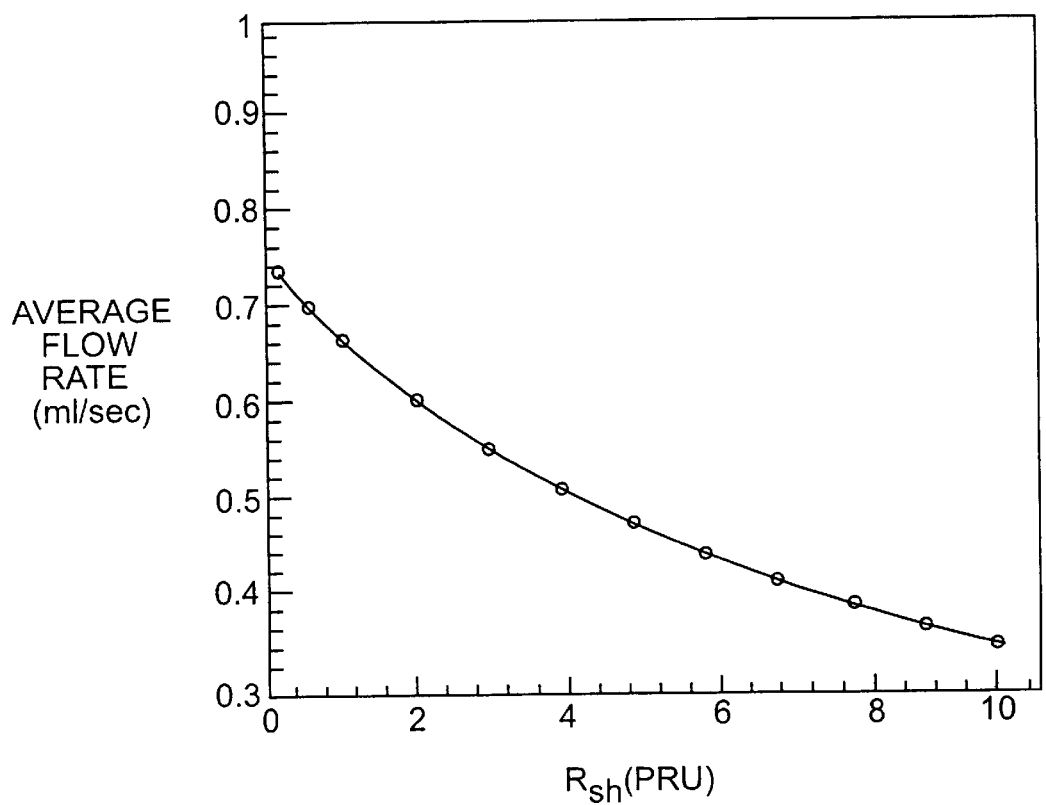
FIG. 7 is a graph showing the relation between the conduit resistance and the flow rate through the conduit when the coronary artery is totally occluded.

To establish the relation between the conduit resistance and the flow rate through the conduit when the coronary artery is totally occluded, a preliminary computation was made and the results are shown in FIG. 7. Before performing these simulations, the values for the coronary artery resistances, $R_{coa}$ (coronary arterioles resistance) and $R_{coc}$ (coronary capillaries resistance), were determined. To determine these flow resistance values, a normal resting total coronary flow of 1 ml/sec is assumed, representing flow through an unoccluded, non-bypassed left anterior descending artery (LAD). However, as the implanted bypass conduit generally will be placed approximately ⅔ of the way down the LAD, it is assumed that the total coronary flow will be ⅔ times the normal flow given above. Thus, the baseline flow rate used to determine $R_{coa}$ and $R_{coc}$ is 0.667 ml/sec, again representing the flow through an unoccluded, non-bypassed artery at a point approximately ⅔ of the way down the vessel. The $R_{coa}$ and $R_{coc}$ values were first altered until this baseline flow rate of 0.667 ml/sec was achieved in an unoccluded LAD, i.e., the stenotic resistance equal to zero. Both resistance values were then increased five-fold to reflect a maximally-dilated state of the peripheral vascular bed in patients with chronic, moderate to severe obstructions so that the maximal flow, with no occlusion and no bypass conduit implanted, would be 3.3 ml/sec. The values were determined, after several trials, to be $R_{coa}=16.5$ and $R_{coc}=1.65$. These values were used throughout the computer simulations.

The model was then run to simulate the flow in a totally occluded artery having a symmetrical resistance bypass conduit implanted. As the results in FIG. 7 are for a totally occluded artery, the flow rate shown in the figure represents both the flow through the shunt and the flow in the artery distal the occlusion. FIG. 7 shows that the calculated flow rate having a symmetrical flow resistance and implanted in a totally occluded artery decreases as the conduit resistance increases. Thus, as the resistance of the conduit approaches infinity, essentially representing a situation in which no conduit is implanted, the flow rate through the artery approaches zero. This result makes sense since there is no blood flow through the total occlusion and also no blood flow through the conduit.

Figures 8A, 8B:
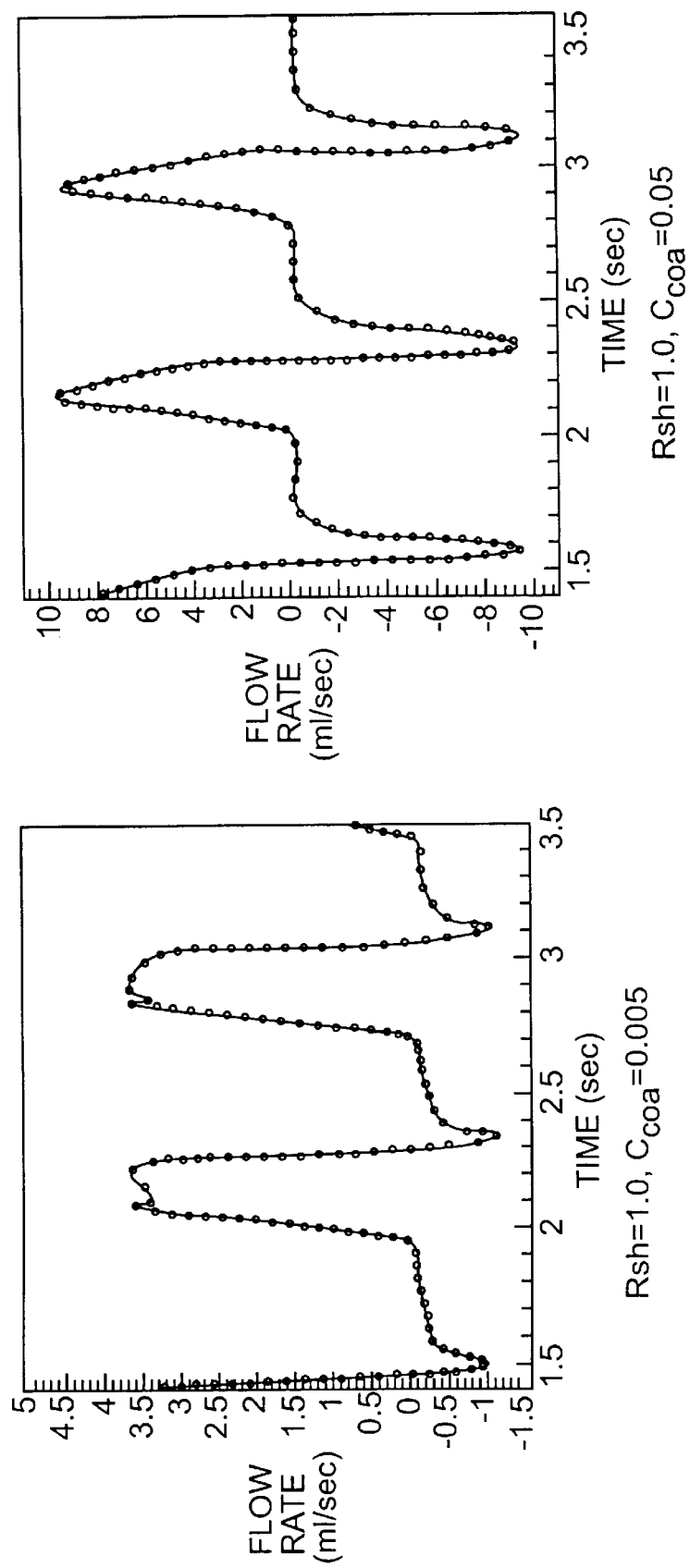
FIG. 8a is a graph of the computed flow rate versus time for a relatively low value of compliance of the coronary artery according to an aspect of the invention.
FIG. 8b is a graph of the computed flow rate versus time for a relatively high value of compliance of the coronary artery according to an aspect of the invention.

FIGS. 8a and 8b show results of the computer simulated flow rate for a lower value ($C_{coa}$=0.005) and a higher value ($C_{coa}$=0.05) of compliance of the coronary artery. The results obtained by altering the compliance of the artery show that while the peak positive and negative flow rates corresponding to the higher compliance are larger than that of those corresponding to the lower compliance value, the net flow rate during one cardiac cycle does not show significant differences between the two cases.

Figure 9:
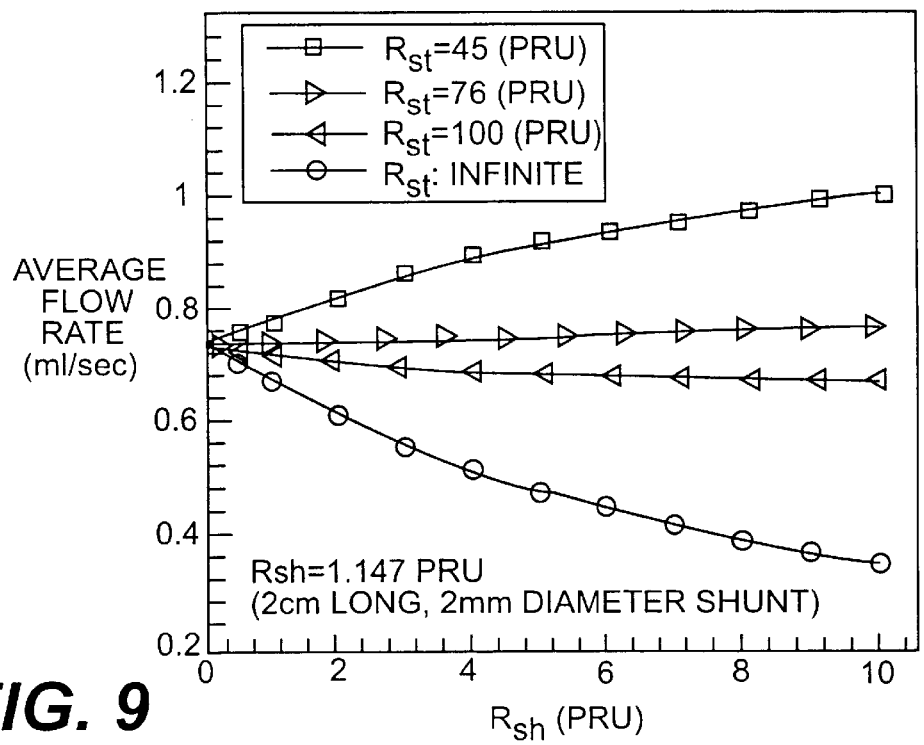
FIG. 9 is a graph of average flow rate versus conduit resistance for various stenotic resistances computed from the computer model according to an aspect of the invention.

Next, the conduit flow resistance was varied and the model was run to explore the effect on total flow in the artery. The shunt resistances were varied for various values of stenotic resistances, as shown in FIG. 9. The first extreme stenotic resistance value simulated, $R_{st}$=45 PRU, corresponds to a relatively low grade stenosed artery. The second extreme stenotic resistance value simulated, $R_{st}$=∞, corresponds to a totally occluded artery. As can be seen in FIG. 9, as the symmetrical resistance of the bypass conduit increases for a totally occluded artery, the flow rate through the coronary artery distal to the occlusion decreases. On the other hand, for a stenosed artery with a resistance value of 45 PRU, as the symmetrical resistance of the bypass conduit increases, the distal flow rate through the coronary artery also increases, essentially reaching an asymptote at a value of slightly over 1 ml/sec as the conduit resistance approaches infinity. Thus, through the use of the model, it has been determined that while a bypass conduit having a symmetrical flow resistance may increase the distal flow rate in a totally occluded artery, it does not help the distal flow rate in the artery for certain degrees of partial occlusion. That is, any increase in flow through the artery that occurs during systole as a result of the bypass conduit is not enough to increase the total coronary flow because of the loss of flow through the bypass conduit that occurs during diastole.

The results of the computer model shown in FIG. 9 also show another important discovery. At a critical stenosis resistance value of approximately 76 PRU the flow rate appears to remain substantially constant regardless of the conduit resistance. Overall, then, for stenotic resistances higher than the critical value, it may be desirable to implant the bypass conduit having a symmetrical resistance. However, for stenotic resistances lower than the critical value, implanting a bypass conduit having a symmetrical flow resistance may lower the total flow through the artery and thus may not be desirable. In other words, there may exist different optimal conduit configurations, yielding different and asymmetrical conduit resistances and ratios of resistance to backflow to resistance to forward flow greater than 1, according to whether the proximal coronary artery is totally occluded or partially occluded. It should be noted that a resistance of 45 PRU represents approximately a 74% diameter reduction, 76 PRU represents approximately a 77% reduction, and 100 PRU represents approximately a 79% reduction, based on estimated diameters of the coronary artery corresponding to the location of the occlusion. The typical average diameter of an unoccluded left anterior descending coronary artery is approximately 3 mm.

Yet another parametric study using the lumped parameter computer model included simulating the distal coronary artery flow for bypass shunts having various flow resistance ratios, i.e., a ratio of the resistance to backflow to the resistance of forward flow. In this portion of the study, the forward and backward resistances of the conduits were varied for different levels of stenotic resistance with a goal of obtaining normal blood flow through the LAD, which is about 1 ml/sec at rest. That is, the conduits modeled for this parametric study included shunts having asymmetrical flow resistances such that the diastolic flow resistance (i.e., in the direction from the coronary artery to the left ventricle) was higher than the systolic flow resistance (i.e., in the direction from the left ventricle to the coronary artery). These types of devices are referred to throughout this application as choke devices, and can be in the form of a conduit, shunt, or stent, or the like. An example of such a choke conduit is shown in FIG. 11, where the shunt has a tapered shape from a relatively small diameter opening in flow communication with the left ventricle to a relatively larger diameter opening in flow communication with the coronary artery distal the occlusion.

Figure 10:
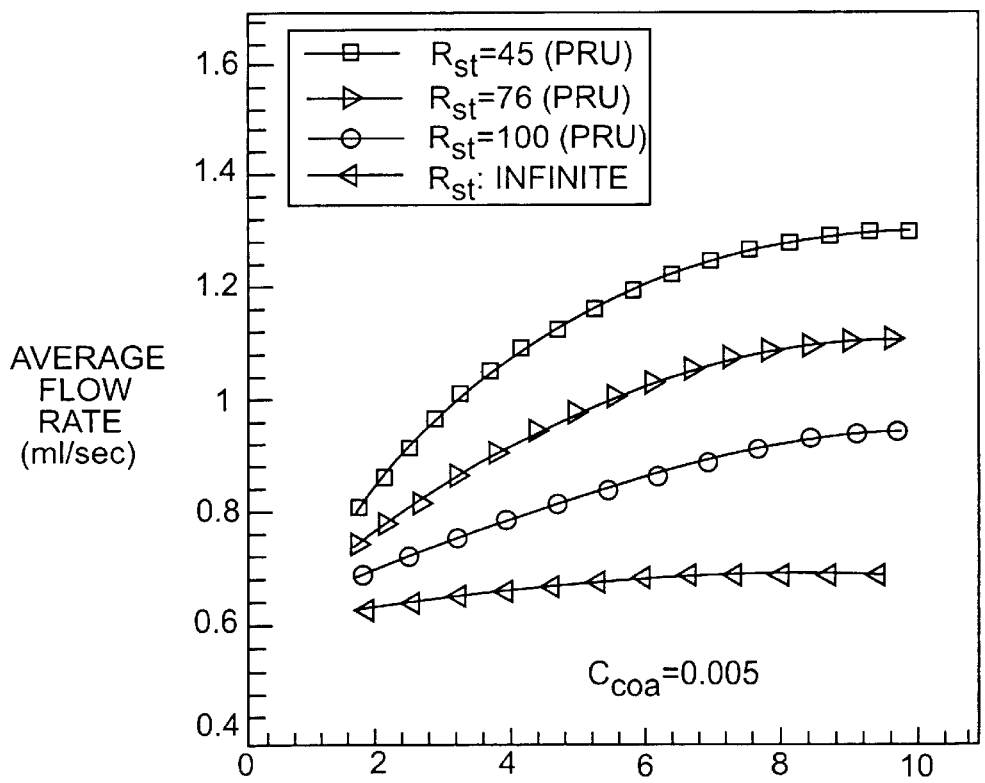
FIG. 10 is a graph of average flow rate versus conduit resistance ratio for various stenotic resistances computed from the computer model according to an aspect of the invention.

As in the parametric study shown in FIG. 9, the coronary blood flow for the case of bypass conduits having asymmetrical flow resistances also was simulated for stenotic resistances in PRU of 45, 76, 100, and ∞, respectively. The results of the simulation are shown in FIG. 10. As can be seen from the graph, as stenotic resistance decreases, the flow rate increases. Moreover, for each stenotic resistance value simulated, as the ratio of backward to forward resistance increases, the mean flow rate increases. However, the incremental increase in flow rate is less as the resistance ratio increases. As also can be seen from the graph shown in FIG. 10, for a partially occluded artery with a stenotic resistance of 45 PRU, a bypass conduit having a resistance ratio of approximately 2 yields a flow rate of about 1 ml/sec, which, as discussed above, represents about the normal flow rate through a non-occluded, non-bypassed artery. Furthermore, for each value of stenotic resistance, there exists a value of the ratio of backward to forward conduit resistance above which the flow exceeds that which would be obtained without implanting a bypass conduit. The maximum mean flow, however, is generally always achieved with the largest values of the resistance ratio. Thus, in designing a conduit to optimize blood flow through the artery, for certain degrees of occlusion, it is desirable to implant a conduit having a resistance ratio of backward to forward flow as large as possible.

Figure 12A:
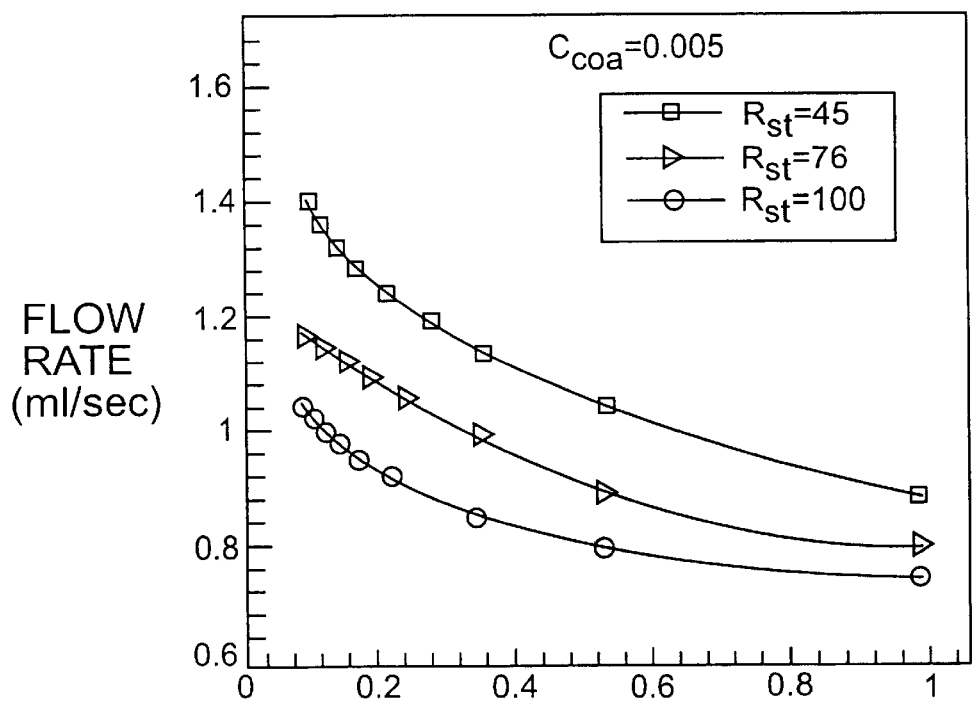
FIG. 12a is a graph of coronary flow rate versus inverse resistance ratio for a heart implanted with a choke conduit and having a coronary artery with a relatively low compliance as computed by the lumped parameter model according to an aspect of the invention.
Figure 12B:
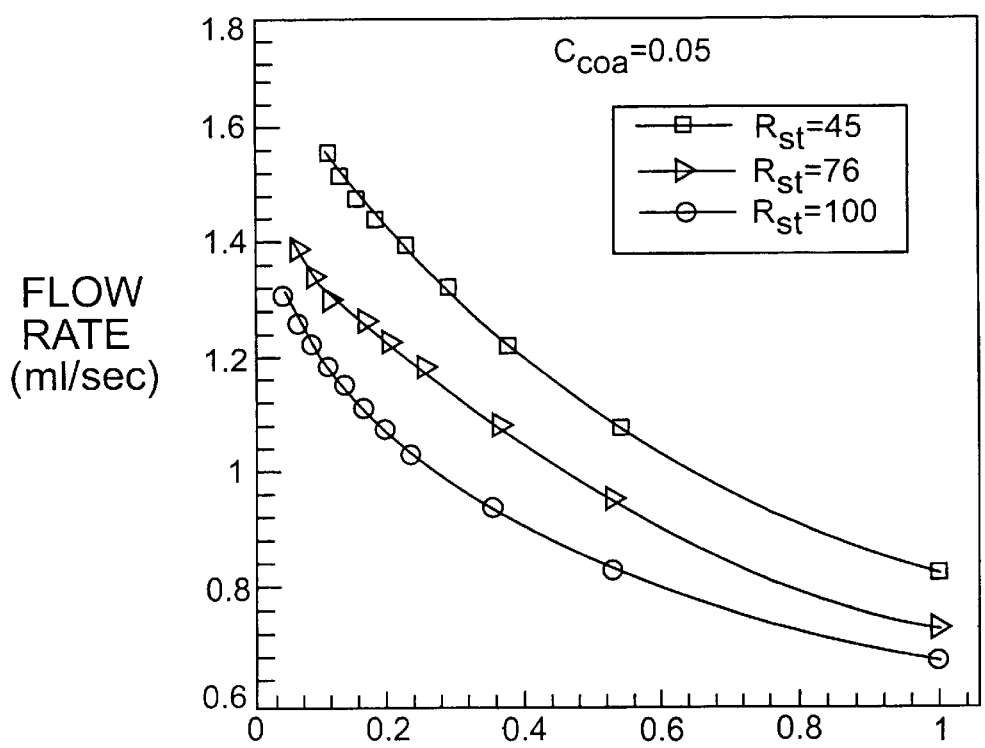
FIG. 12b is a graph of coronary flow rate versus inverse resistance ratio for a heart implanted with a choke conduit and having a coronary artery with a relatively high compliance as computed by the lumped parameter model according to an aspect of the invention.

FIGS. 12a and 12b show the effect of the compliance of the coronary artery on the choke conduit simulation. In FIG. 12a, the lower compliance, i.e., capacitance ($C_{coa}$=0.005 ml/mmHg) results are shown and in FIG. 12b, the higher compliance, i.e., capacitance ($C_{coa}$=0.05 ml/mmHg) results are shown. In the graphs in FIGS. 12a and 12b, the resistance ratio plotted is the inverse of that in FIG. 10, that is, the ratio of forward flow resistance to backward flow resistance. However, the conduits modeled in this study are the same as those in FIG. 10 in that the resistance to backward flow is higher than the resistance to forward flow. The results of the simulation in FIGS. 12a, and 12b show that as the compliance, or capacitance, of the artery increases, the flow rate in the artery is higher than for a lower compliance of the artery at the same bypass conduit resistance ratio. Also, the gradient of the flow rate increase is steeper for the case of higher compliance than for the case of lower compliance. Thus, to the extent that compliance can be controlled, some additional gains in coronary flow may be achieved by increasing the compliance.

Figure 11:
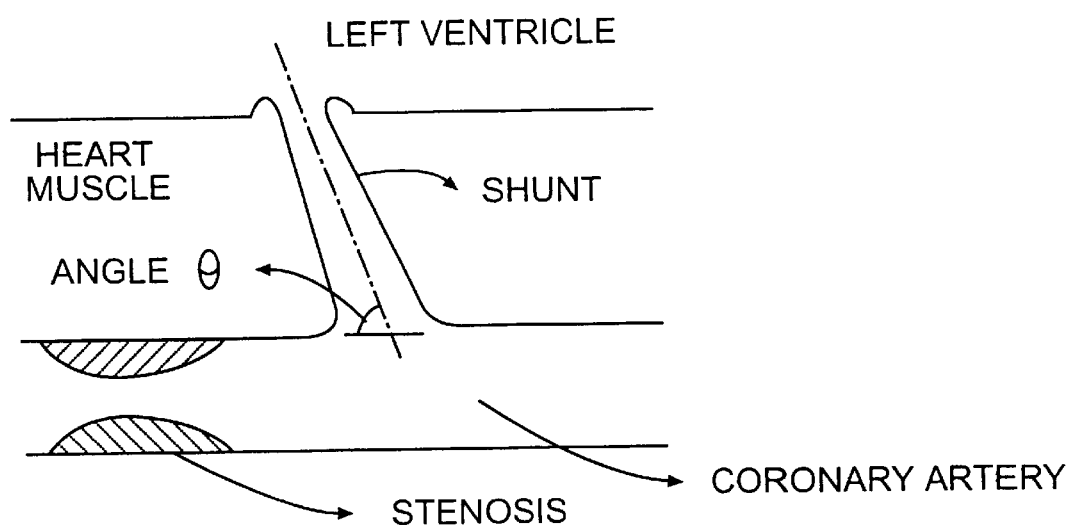
FIG. 11 is a cross-sectional view of a choke conduit according to an aspect of the invention.

In addition to performing parametric studies using the lumped parameter computer model, a three-dimensional fluid dynamic computation analysis for a bypass conduit design similar to that shown in FIG. 11 was performed. The purpose of this fluid dynamic analysis was to examine the influence of geometry of the device to optimize total coronary perfusion. The simulation was performed using a commercially available finite element package, ADINA (Automatic Dynamics Incremental Nonlinear Analysis). A mixed displacement/pressure-based finite element formulation was used to solve the governing fluid dynamic equations. For the boundary condition, the simulation results from the lumped parameter model of the coronary circulation with the artery totally blocked were used. The time-varying pressures and flow rates at the left ventricle obtained from the lumped parameter model simulation were applied to the bypass conduit inlet boundary. The governing equations used for the fluid dynamic analysis are the Navier-Stokes equations for viscous incompressible flow obtained from the principles of conservation of mass and momentum.

Figure 13:
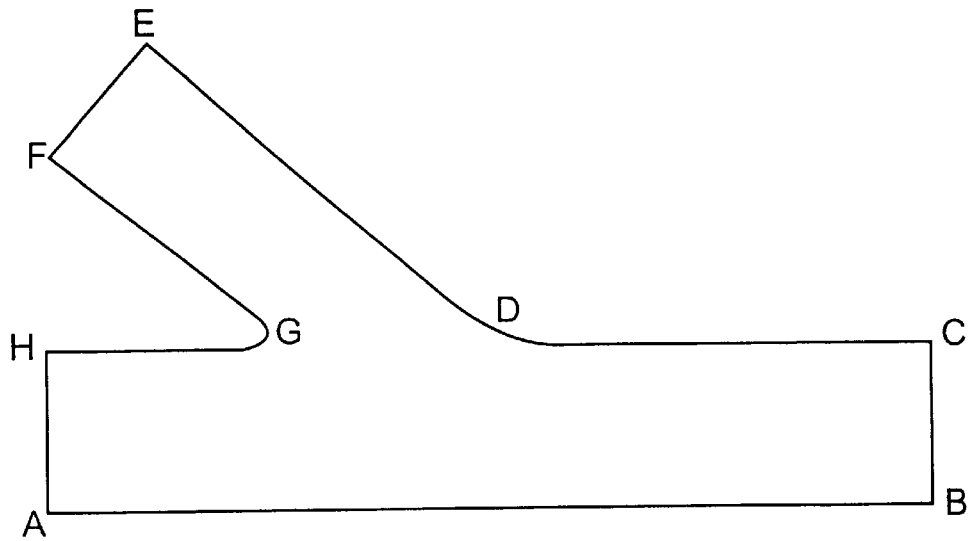
FIG. 13 is a schematic diagram of the geometry and boundary conditions used to perform a fluid dynamic analysis of a conduit according to an aspect of the invention.

As mentioned above, a three-dimensional model (as shown, for example, in FIGS. 14a and 14b) was used to simulate blood flow in the coronary bypass conduit. Two implant angles, 30° and 90°, as measured with respect to the direction of blood flow in the coronary artery, were modeled. Each conduit included a tapered configuration from a relatively small diameter in flow communication with the left ventricle to a relatively larger diameter in flow communication with the coronary artery. As explained above, this tapered configuration forms a choke conduit having an asymmetrical flow resistance. The detailed geometry and boundary conditions are illustrated schematically in FIG. 13. The fluid modeled was blood having a viscosity of 0.003 kg/(m-s) and a density of 1000 kg/m$^3$. For the boundaries E-F and B-C, the time-dependent pressure boundary conditions derived from the system simulation of the coronary circulation were imposed. In obtaining the boundary conditions from the lumped parameter model simulation, an infinite value for the stenotic resistance was used.

Figure 14A:
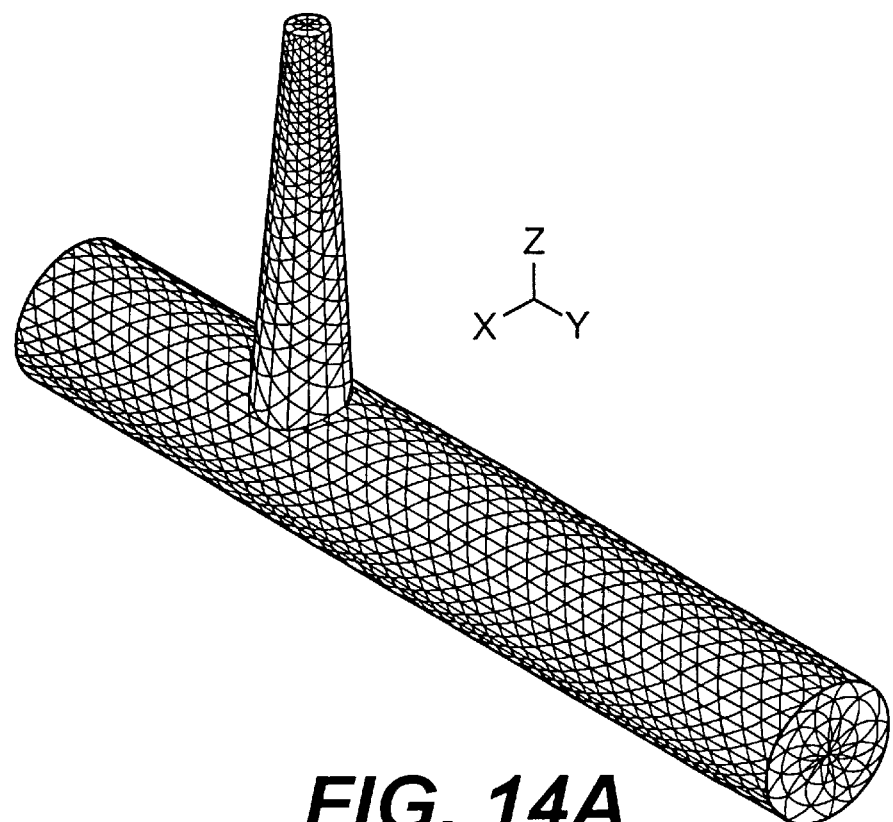
FIG. 14a is a perspective view of a mesh model of a conduit used for a fluid dynamic analysis according to an aspect of the invention.
Figure 14B:
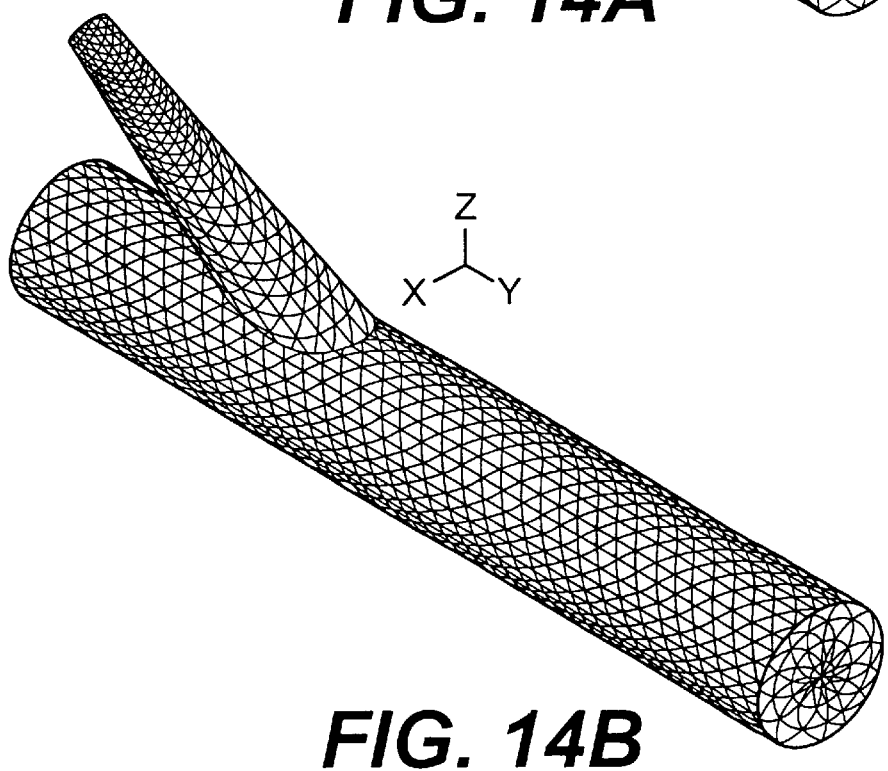
FIG. 14b is a perspective view of a mesh model of a conduit used for a fluid dynamic analysis according to another aspect of the invention.
Figure 15A:
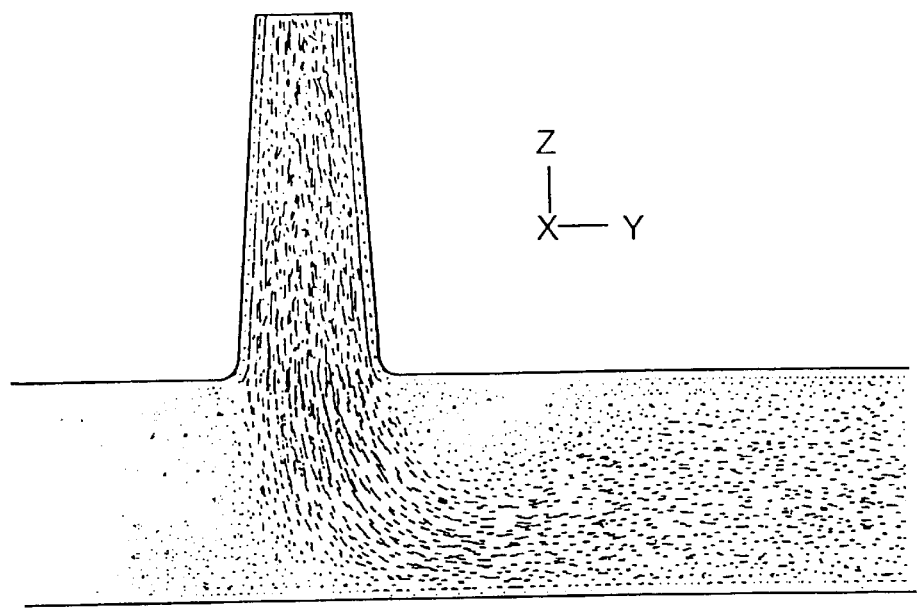
Figure 15B:
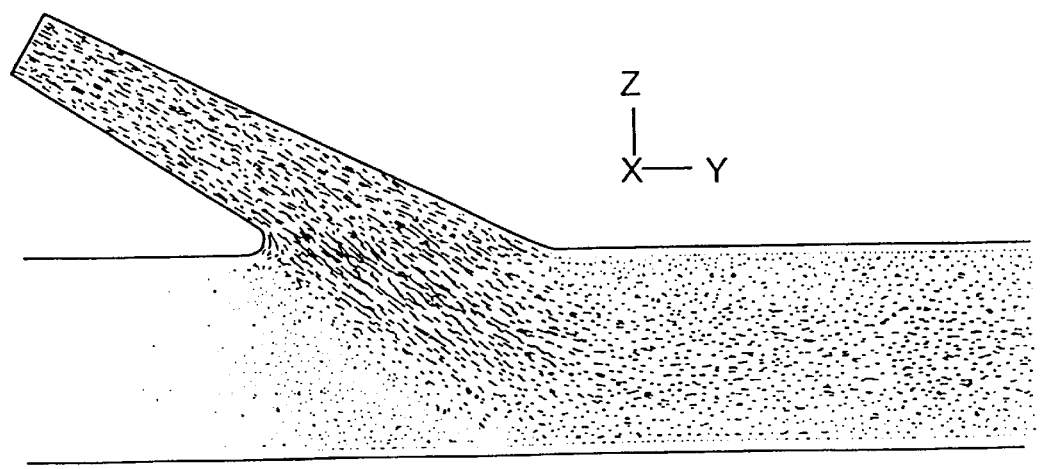
FIG. 15b is a vector velocity plot of the fluid dynamic analysis performed for the conduit shown in FIG. 14b.

The surface mesh of the bypass conduits used for the fluid dynamic analysis are shown in FIGS. 14a and 14b. FIG. 14a shows the bypass conduit angled at 90° to the direction of blood flow in the coronary artery, while FIG. 14b shows the bypass conduit angled at 30° to the direction of blood flow in the coronary artery and angled to direct the blood downstream of the occlusion. The results of the fluid dynamic analysis are shown in the velocity vector plots of FIGS. 15a and 15b. These results correspond to a point in the cardiac cycle when left ventricle reaches approximately its peak pressure and correspond to each of the bypass shunt geometries shown in FIGS. 14a and 14b, respectively. For the 90° case shown in FIG. 15a, a strong recirculating region near the intersection of the conduit with the coronary artery results from the separation of blood flow from the wall. On the other hand, for the 30° case shown in FIG. 15b, there is no separation except in the region corresponding to the location of the occlusion. Since recirculating regions or regions of low shear stress are often associated with thrombus or clot formation, the smaller angle would be beneficial in preventing occlusion of the shunt.

Experiments with Various Bypass Conduit Configurations

As the simulation of coronary blood flow using the lumped parameter model indicates, to optimize total coronary artery flow for certain levels of partially occluded arteries, it is preferable to implant a bypass conduit having an asymmetrical flow resistance. That is, the preferred bypass conduit in these cases of stenosed arteries will have a greater resistance to diastolic flow through the conduit from the coronary artery to the left ventricle than to systolic flow through the conduit from the left ventricle to the coronary artery. It is desirable, according to an aspect of the invention, that the bypass conduits having such asymmetrical flow resistances do not require the use of valves and other mechanical flow control mechanisms. Rather, it is preferable to obtain such asymmetrical flow resistances through the use of passive flow control mechanisms such as the geometrical configuration of the conduit, the geometry of the implant of the conduit, and other like characteristics.

To determine whether the geometries and design characteristics of various conduits could produce the desired asymmetrical flow resistances, a series of experiments were conducted using various conduit flow path configurations and implant configurations. The experiments included testing the various conduit configurations shown in FIGS. 16a–16c. The conduit configuration shown in FIG. 16a includes a smaller diameter opening in flow communication with the left ventricle and a larger diameter opening in flow communication with the coronary artery. Tests were conducted on a conduit according to the configuration FIG. 16a with smaller diameters of 0.040 in. and 0.052 in. Both of these conduits had a larger diameter of 2 mm and a length of 2 cm. Both the 0.040 in. and 0.052 in. smaller diameter conduits of FIG. 16a taper inward slightly from the left ventricle with a radius of curvature R at the inwardly tapered portion of 0.010 inches. After tapering inward slightly, the conduits then taper outward at an angle a3 of 4°, as measured with respect to the longitudinal axis of the conduit, to the larger diameter end of the conduits. The conduit configuration shown in FIG. 16b has a constant inner diameter of 2 mm and a length of 2 cm. The conduit configuration shown in FIG. 16c has a larger diameter opening in flow communication with the left ventricle tapering to a smaller diameter opening in flow communication with the coronary artery. The larger opening has an inner diameter of 6 mm, the smaller opening has an inner diameter of 2 mm, and the length of the conduit is 2 cm.

The total resistance of a given bypass conduit implanted between the left ventricle and coronary artery results from the sum of three component resistances. The first resistance corresponds to the resistance occurring in the transition zone of the flow path between the ventricle and the lumen of the conduit. The second resistance corresponds to resistance to flow of the lumen itself. The third resistance corresponds to the resistance to flow occurring at the transition between the lumen flow path and the coronary artery. Thus, aside from varying the configuration of the lumen of the conduit, varying the configurations of the various transition zones between the conduit and the left ventricle and the conduit and the coronary artery may influence the backward and forward resistances of the conduit.

Figure 16A:
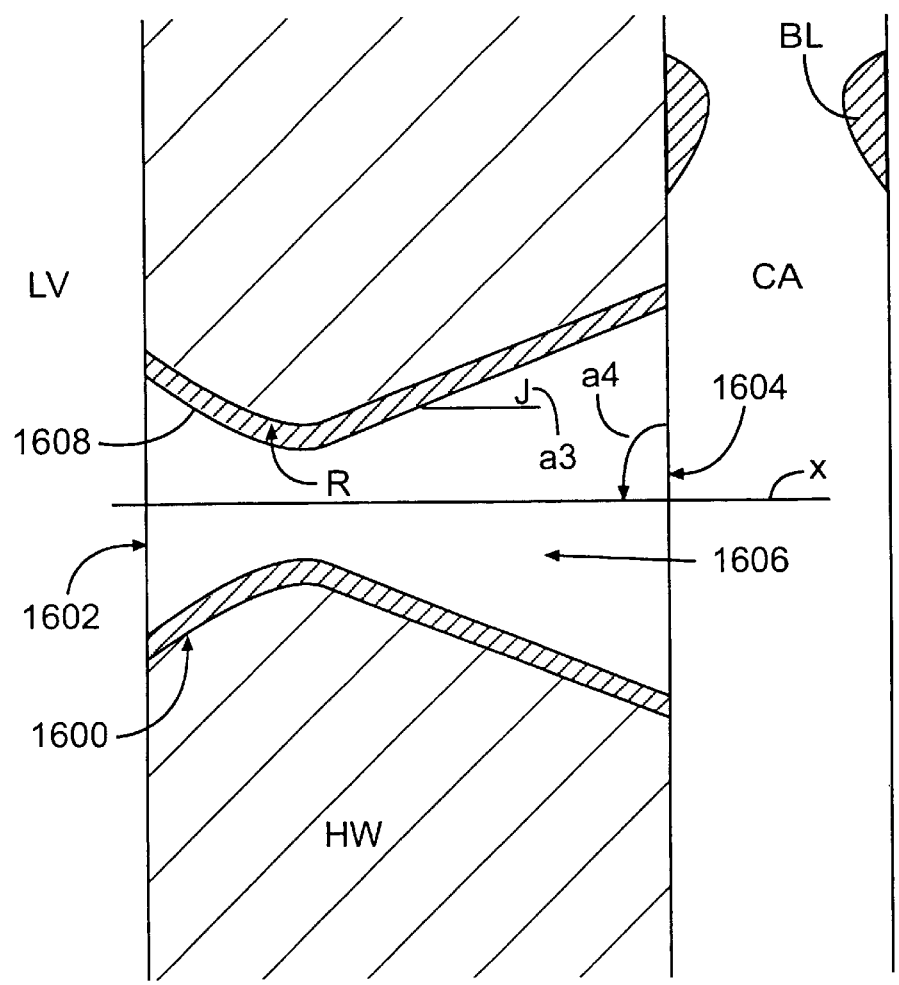
FIG. 16a is a cross-sectional view of a conduit having an asymmetrical flow resistance with a backward flow resistance greater than a forward flow resistance according to an aspect of the invention.
Figure 16B:
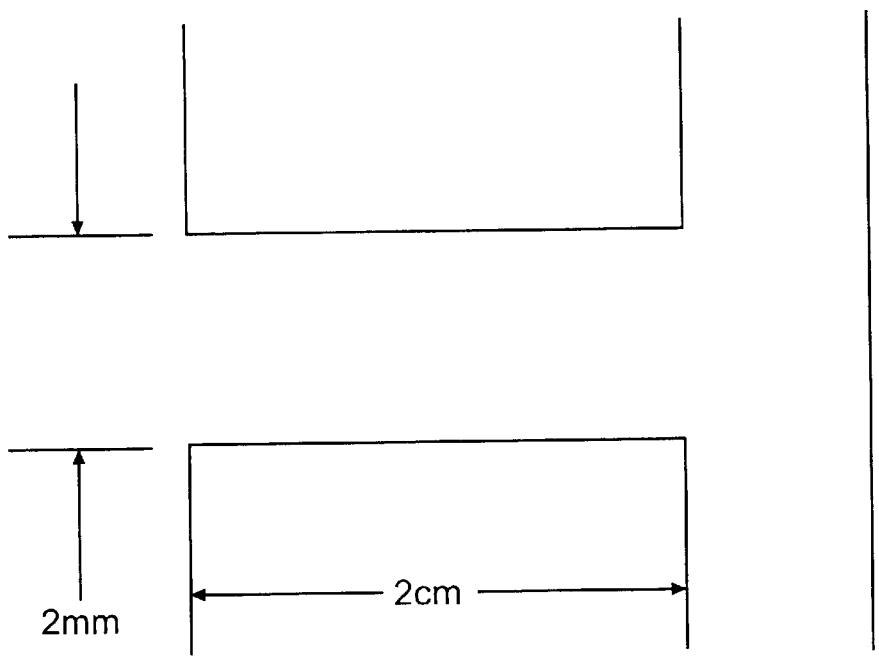
FIG. 16b is a cross-sectional view of a conduit having a symmetrical flow resistance of approximately 1.147 PRU according to an aspect of the invention.
Figure 16C:
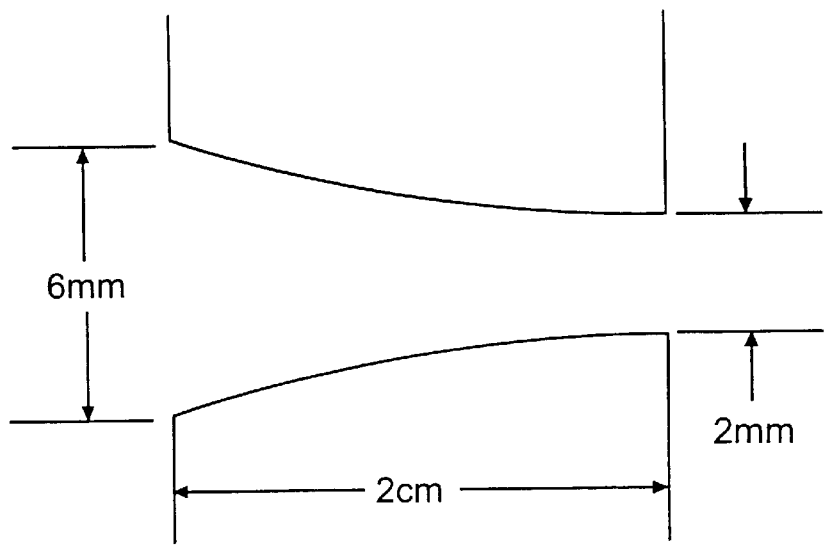
FIG. 16c is a cross-sectional view of a conduit having a funnel configuration which was used in experiments according to an aspect of the invention.
Figure 17A:
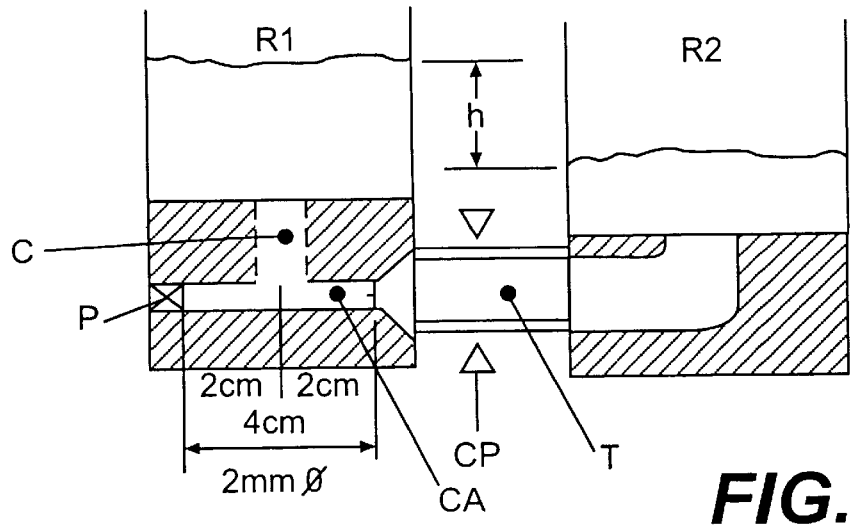
FIG. 17a is a cross-sectional view of a 90 degree entry experimental setup for testing conduits according to an aspect of the invention.
Figure 17B:
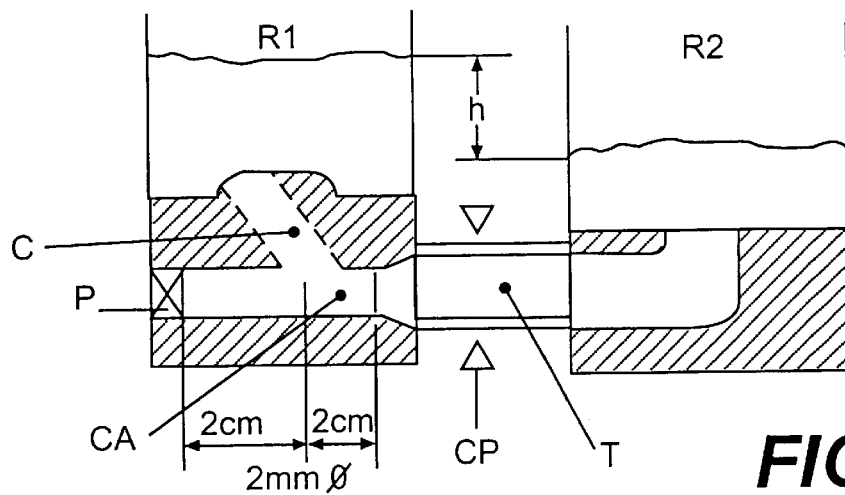
FIG. 17b is a cross-sectional view of a 30 degree entry experimental setup for testing conduits according to an aspect of the invention.
Figure 17C:
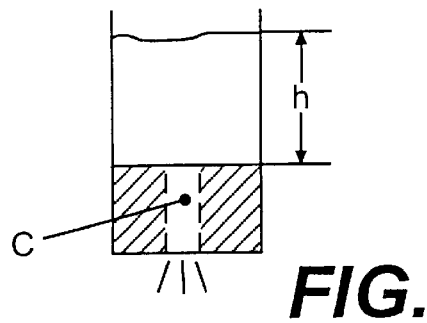
FIG. 17c is a cross-sectional view of a stent only experimental setup for testing conduits according to an aspect of the invention.

FIGS. 17a–17c show three different test setups used in the experiments resulting in various transition zone configurations. FIG. 17a shows a test setup used to simulate a right angle junction between the artery, represented by the flow path CA in the figure, and the conduit flow path C (designated "90 deg entry" in the results shown in FIGS. 18a–18c and 19). FIG. 17b shows a test setup used to simulate a 30 degree junction between the artery CA and the conduit flow path C (designated "30 deg entry" in the results shown in FIGS. 18a–18c and 19). FIG. 17c shows an idealized test setup which has no junction at all (designated "stent only" in the results shown in FIGS. 18a–18c and 19). Each of the various transition zone configurations shown in FIGS. 17a–17c were not necessarily tested with each of the conduit configurations shown in FIGS. 16a–16c.

In each experiment, the conduit flow paths were machined into a polycarbonate block. For the 90 degree and 30 degree entry setups, the conduit flow path to be tested was connected between two reservoirs, R1 and R2, as shown in FIGS. 17a and 17b, respectively. A section of silicone rubber tubing T was used to make one of the connections and a clamp CP was placed on the tubing to respectively permit and prevent or hinder flow through the conduit flow path. A plug P was placed in the coronary artery upstream of the junction between the conduit and the artery. Initially, one of the reservoirs was filled with enough water to prime the flow path and the other was filled with enough water to achieve the desired initial pressure across the flow path. Initial water levels in each reservoir were recorded. For each of the test setups the pressure driving the flow through the conduit was calculated as $\Delta P = \rho gh$. The silicone rubber tubing T was then unclamped and a timer was started. Between 20 and 100 mls of water was allowed to flow through the stent. After this water flowed through the stent flow path, the tube T was clamped and the time stopped and final water levels in each reservoir were recorded. This process was repeated until the water levels in each reservoir were close enough to one another that the resultant flow was 20 ml/min or less. Data were entered into a spreadsheet and flow rates and average pressure differentials for each data point were calculated.

Figure 18A:
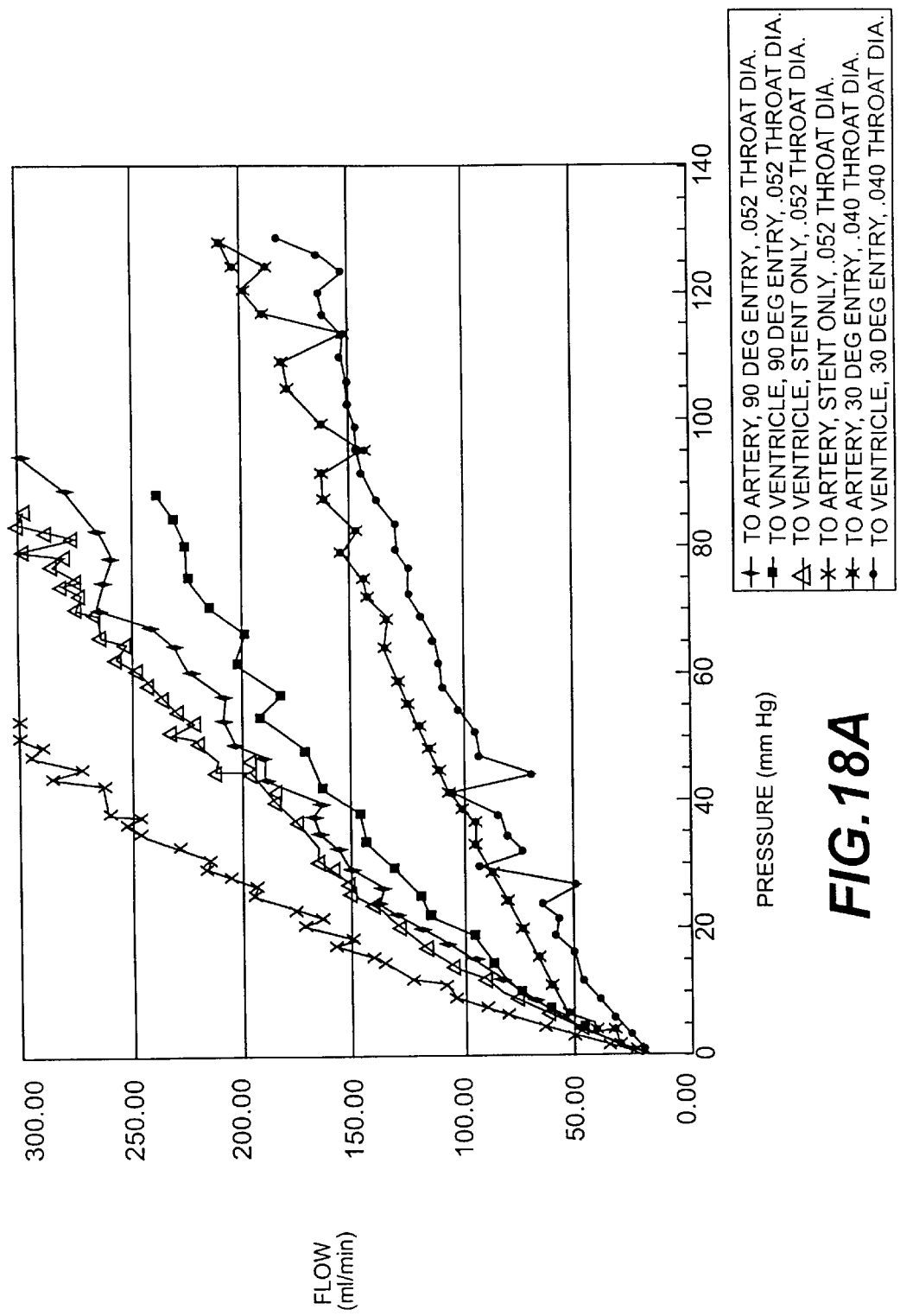
Figure 18B:
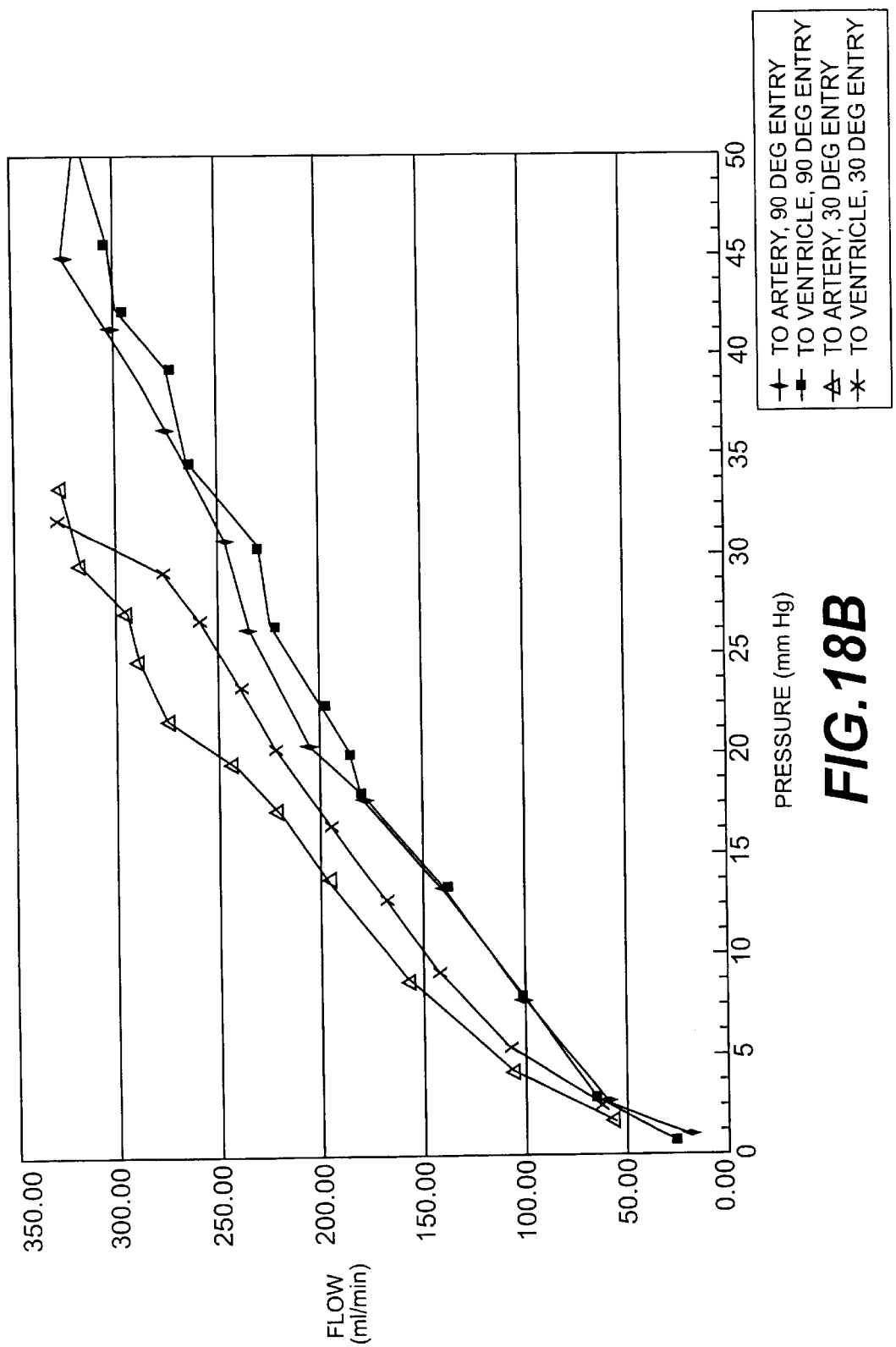
FIG. 18b is a graph of experimental results of flow versus pressure corresponding to experiments using the conduit of FIG. 16b.
Figure 18C:
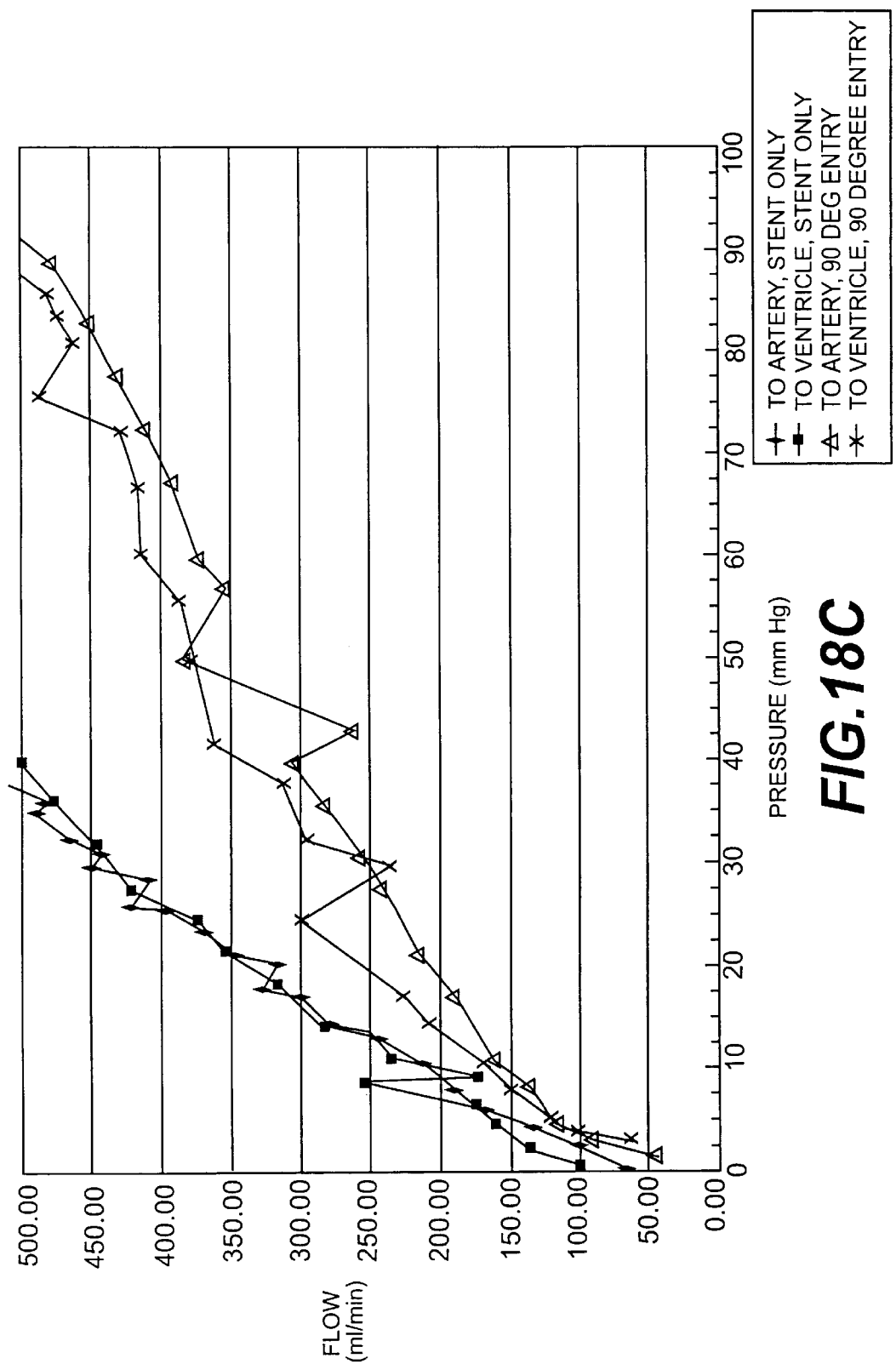
FIG. 18c is a graph of experimental results of flow versus pressure corresponding to experiments using the conduit of FIG. 16c.

Results of the experiments are shown in FIGS. 18a–18c and 19. FIGS. 18a–18c show plots of pairs of lines corresponding to forward and backward, or reverse, flow versus pressure for a specific conduit flow path configuration or artery junction setup. Thus, in FIG. 18a, the results of the experiment obtained using a conduit flow path geometry for the 90 degree entry setup (FIG. 17a) and the conduit only setup (FIG. 17c) included a smaller opening inner diameter of 0.052 in., whereas for the 30 degree entry setup (FIG. 17b) the smaller opening inner diameter was 0.040 in. The 0.052 in. inner diameter was necessary due to fabrication requirements of those configurations. The smaller inner diameter for the 30 degree entry case results in a greater overall resistance. As shown in FIG. 18a, in each case, the resulting forward or "to artery" flow is greater than the reverse or "to ventricle" flow for a given pressure. If all of the conduit flow path configurations used to obtain the results in FIG. 18a were the same, curves for the 30 degree entry case would be expected to lie between the conduit only and the 90 degree entry case. These results show that, while the degree of asymmetry is relatively small, tapered conduits can be designed with asymmetric flow resistance, and that the more favorable configurations are those that have a relatively small diameter on the ventricular side compared to that on the end attached to the coronary artery. Rounding at the ends of the conduit, especially at the ventricular end, help to reduce the pressure drop during forward flow, as does a smooth entry into the coronary artery. The trade-off is that the tapered shunts with asymmetric resistance might also have a higher mean flow resistance. The analysis helps to take all these factors into account to determine the optimal configuration for a given situation.

Similar results as those in FIG. 18a are shown in FIGS. 18b and 18c for the conduit flow path configurations corresponding respectively to FIGS. 16b and 16c. The results of the so-called "funnel configuration" shown in FIG. 16c are plotted in FIG. 18c. As shown in this figure, this conduit flow path configuration resulted in the lowest overall mean resistance. Additionally, the flow rate through the conduit remained approximately the same for both directions, that is, toward the ventricle and toward the artery. An experiment with the funnel configuration for a 30 degree entry was not performed due to the relatively symmetric resistances resulting with the 90 degree entry and conduit only setups. Thus, FIG. 18c only contains two pairs of plotted lines.

FIG. 18b shows the flow versus pressure results for the conduit flow path configuration of FIG. 16b. This conduit configuration is in the form of an essentially straight tube having a constant 2 mm inner diameter. Experiments using this conduit flow path configuration were only performed for the 30 degree and 90 degree setups. As can be seen from the graphs of flow versus pressure in FIG. 18b, when the straight tube enters the artery at a 30 degree angle to the direction of blood flow in the artery, a noticeable difference in flow rate between the forward (i.e., to artery) and backward (i.e., to ventricle) flow directions results. Although the difference is not as pronounced as in flow path configuration of FIG. 16a, it is measurable. Furthermore, the overall flow resistance of the simple tube configuration is lower than that of the configuration of FIG. 16a. For the 90-degree setup, the simple tube flow path configuration of FIG. 16b resulted in little difference in flow rate between the forward and backward flow directions. This small asymmetry in resistance is likely associated with the turbulence formed by the jet of blood entering the ventricle, leading to asymmetry in the resistance to flow.

The computer simulated parametric flow studies discussed above characterized the simulated conduit models in terms of flow resistance ratios, in addition to the overall conduit resistance. More specifically, the flow resistance ratio is the ratio of the resistance to backward flow from the coronary artery to the left ventricle during diastole to the resistance to forward flow from the left ventricle to the coronary artery during systole. From the computer studies, it was determined that a large resistance ratio produces the greatest distal coronary artery flow rate for any level of stenosis or for total occlusion of the artery. However, when the coronary artery is partially occluded to a level such that the stenotic resistance is 45 PRU, the asymmetric resistance can make the difference between a bypass conduit that may not benefit the patient and one that would. A bypass conduit having a resistance ratio of at least approximately 2 can thus be expected to result in a relatively good perfusion of the heart tissue.

Using the graphs in FIGS. 18a–18c, rough calculations of the experimentally measured resistance ratios can be made. Since the flow vs. pressure curves are slightly non-linear, the ratio is a relatively weak function of flow rate. For consistency, resistance ratios are calculated at 100 ml/min and 200 ml/min for each set of experimental results contained in FIGS. 18a–18c. These flow rates are chosen since they represent rough approximations to the average and peak arterial flow rates. The results of the resistance ratio calculations are found in tabulated from in FIG. 19. It should be noted that for the 30 degree entry case of the conduit flow path configuration of FIG. 16a, a flow rate of 200 ml/min was slightly beyond the upper end of what could be achieved with the experimental set up and the relatively high flow resistance of the conduit with a 0.040 in. smaller opening inner diameter. Therefore, the resistance ratio was calculated at a flow rate of 150 ml/min instead. In reviewing the tabulated results shown in FIG. 19, the highest calculated resistance ratio was 1.6, which corresponded to the conduit configuration of FIG. 16a and the conduit only configuration. As mentioned above, however, this setup is an idealized situation and one that cannot be achieved when the conduit is implanted into the heart, as there will be a junction between the conduit and the coronary artery. However, this configuration achieved the highest resistance ratio of those configurations tested and this resistance ratio approached the desired value of 2 and thus is a promising result.

The tabulated results of FIG. 19 also show that resistance ratios of 1.2 and 1.3 were obtained for the flow path configurations of FIG. 16a with a 90 degree entry setup and a 30 degree entry setup, respectively. For the simple tube configuration (i.e., "Constant I.D."), the tabulated results show that for the 30 degree entry setup, resistance ratios of up to almost 1.4 can be obtained. Overall, the experiments show that a measurable difference in flow resistance as a function of direction of flow in the conduit can be obtained without the need of a check valve or the like. Rather, the conduit can be designed and implanted such that a passive flow control is achieved by varying characteristics such as, for example, the degree of taper of the conduit, the diameters of the ventricle and artery openings, and the geometry of the implantation of the conduit in the heart wall between the left ventricle and coronary artery. The experimental results also seem to indicate that, in general, higher resistance ratios may come at the expense of higher overall flow resistances. This should be considered when choosing a conduit design.

Figure 27:
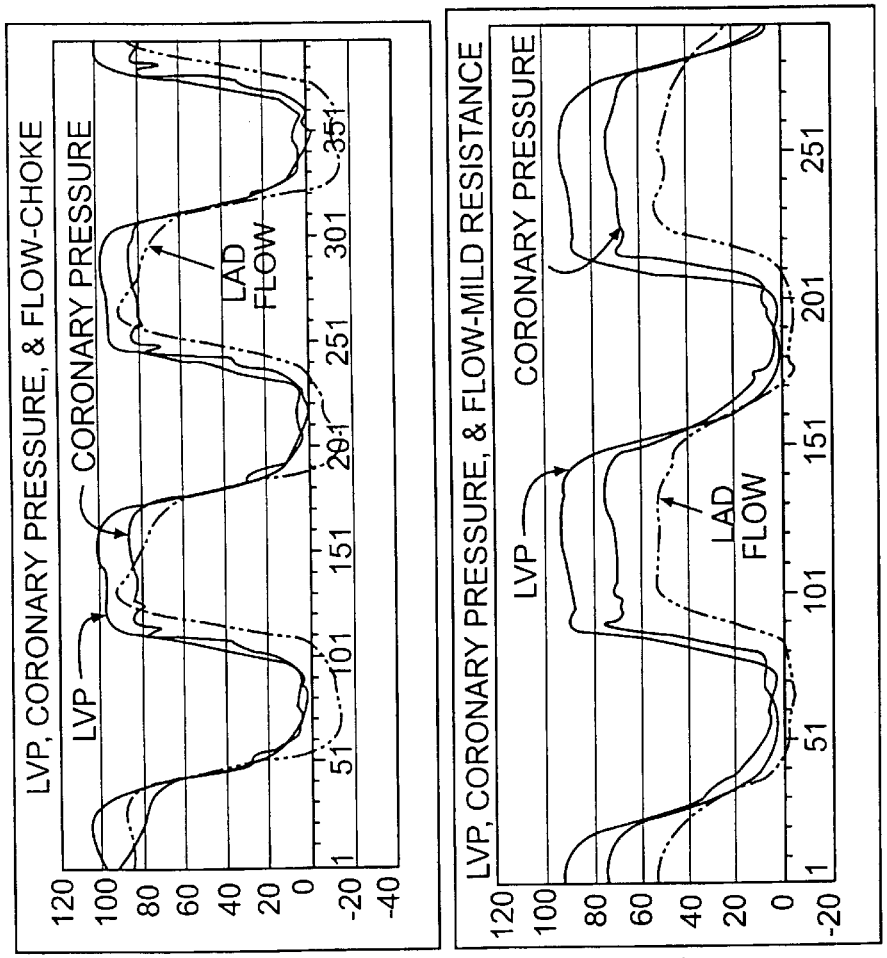
FIG. 27 is a table of results and parameters of experiments in dogs using different bypass conduit configurations.

Further experiments were performed to examine the effects of different stent (or conduit) resistances on actual coronary blood flow. The conditions and results of these experiments are shown in FIG. 27. A choke device having a higher reverse flow resistance (i.e., diastolic flow resistance) than forward flow resistance (i.e., systolic flow was tested with the coronary artery pressure similar to the left ventricle pressure, i.e., high in systole and low in diastole. Using this choke device, coronary blood flow was almost equal to flow under baseline conditions (39.97 ml/min versus 43.49 ml/min). Using a conduit having a mild symmetric resistance, total coronary blood flow decreased to 27.71 ml/min. However, negative diastolic flow was almost zero. These results also confirm that mean coronary blood flow can be significantly increased through the use of an asymmetric conduit.

Conduit Configurations for Passive Flow Control

As has been discussed above, one of the advantages of certain embodiments of the conduits of the present invention is that they can be designed to passively optimize fluid or blood flow through them. That is, the design or configuration of a conduit may be such that it passively achieves flow control without microvalves, check valves, or other active or movable devices that stop flow through the conduit, either partially or completely, during at least a portion of the cardiac cycle. Such passive flow control can be designed into the geometry, configuration or features of a conduit so that it biases flow in one direction or the other. Thus, flow within and/or completely through the conduit may occur in either direction (whether simultaneously or severally), but net flow in the desired direction can be maximized by maximizing flow in that direction and/or minimizing flow in the opposite direction. Such passive flow control mechanisms may comprise, for example, tapers in the lumen or a changing inner diameter of the conduit, tapers and/or radii of curvature at the openings of the conduit, the angle of insertion of the conduit with respect to the axis of the coronary artery (or direction of blood flow in the artery), and other similar conduit design characteristics or implantation characteristics.

As discussed above, in one preferred embodiment, flow control is achieved by maximizing flow through the conduit in one direction (preferably from the left ventricle to the coronary artery), but minimizing flow through the conduit in the opposite direction. In other words, in one embodiment, it is advantageous to have a low conduit resistance in the forward direction (from the left ventricle to the coronary artery), but a higher resistance in the opposite direction. In that sense, the conduit acts as a type of choke device having a higher reversed flow resistance or diastolic resistance than the forward flow or systolic resistance.

Figure 20:
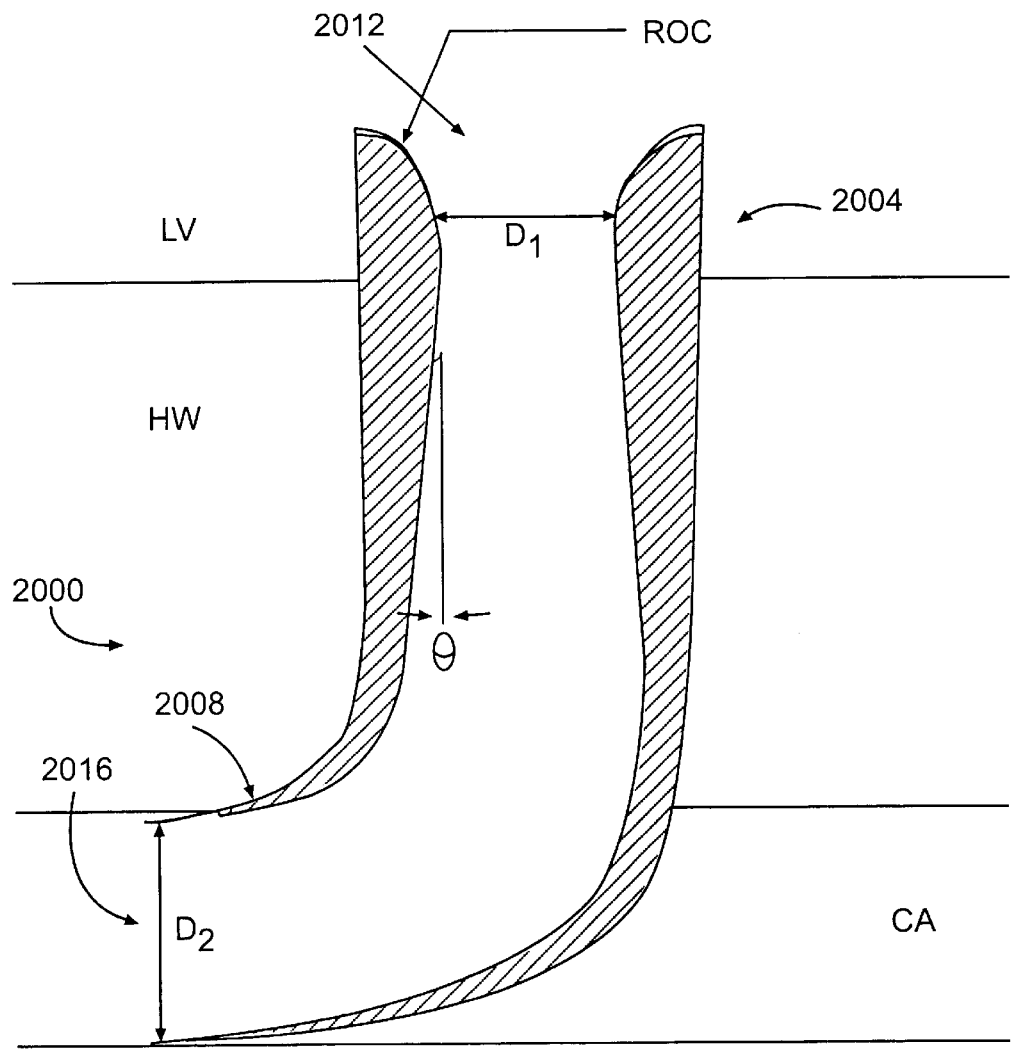
FIG. 20 is a cross-sectional view of an embodiment of a conduit having an asymmetrical flow resistance with the backward resistance higher than the forward resistance according to an aspect of the invention.

Referring to FIG. 20, a schematic, cross-sectional view a conduit 2000, designed to achieve flow optimization under certain circumstances, and which has an asymmetrical flow resistance, is shown. In this case, the conduit 2000, implanted in the heart wall HW, generally is curved with a varying wall thickness, and has a proximal end 2004 configured to extend into the left ventricle LV. A distal end 2008 curves so that its exit is approximately transverse to the direction of flow in the distal portion of the coronary artery CA. In this context, the term "distal" is used with respect to direction of desired flow and represents a location downstream from a given point in the flow path. It will be observed that the proximal portion of the conduit 2000 shown in FIG. 20 preferably extends into the left ventricle LV to take into consideration the changing wall thickness of the myocardium. Thus, the proximal portion of the conduit 2000 may extend into the ventricle LV roughly 5%–30% to accommodate for such changing wall thicknesses. During systole, the-myocardium HW contracts, thus increasing the thickness of the myocardium. The conduit 2000 of FIG. 20 is designed to accommodate such a thickening such that its entrance 2012 will be approximately flush with the internal surface of the myocardium HW during systole.

Also, the proximal end 2004 of the conduit 2000 at the entrance 2012 is shaped so as to have a high radius of curvature, which is approximately ½ of the difference between the diameter at the exit 2016 and the diameter of the conduit 2000 at the entrance 2012, i.e. ROC $=(D_2-D_1)/2$, as shown in FIG. 20. This curvature tends to reduce flow losses (or in other words, decreases resistance to flow) at the entrance 2012 as flow enters from the ventricle, thereby maximizing flow through the conduit during systole. At the same time, the decreased diameter at the entrance 2012 increases the resistance to reverse diastolic flow at that location by producing a high speed turbulent jet that dissipates energy on entry into the ventricular chamber, thus tending to decrease negative flow through the conduit 2000 or flow from the coronary artery CA back into the ventricle LV. Thus, the proximal portion of the conduit 2000 is designed so as to achieve an abrupt expansion resulting in large exit losses and consequently high resistance to diastolic flow. In addition, the wall thickness of the conduit 2000 varies by a taper ($\theta$) of approximately 40, thus producing the differences in entrance and exit diameters. This degree of taper tends to minimize losses in a gradual conical expansion region.

At the distal end 2008, on the other hand, flow losses are minimized, so as to minimize flow resistance. Such exit losses are essentially zero because the exit diameter of the conduit 2000 approximates or matches the diameter of the coronary artery CA. Moreover, during diastolic flow, there will be losses at the exit of the conduit 2000, thus increasing the resistance to such negative flow. The curved configuration of the distal end 2008 of the conduit 2000 also minimizes flow loss during diastole resulting from proximal flow through a partial occlusion. In other words, the distal end 2008 of the conduit 2000 can be constructed so as to allow a proximal flow passing a partial occlusion and contributing to the flow through the conduit 2000 to produce an advantageous total coronary flow rate. Examples of such distal end configurations that allow a proximal flow passing a partial occlusion to contribute to the flow through the conduit are described in PCT/US99/20484, filed Sep. 10, 1999 and published Mar. 23, 2000 as WO 00/15146, the disclosure of which is incorporated by reference herein. Such distal designs for the conduit 2000 are described elsewhere herein and are compatible with the conduit of FIG. 20. Moreover, the conduit 2000 can be constructed from a rigid or flexible material, it may be a solid wall or lattice structure (e.g., stent-like) as described below.

Thus, the conduit 2000 of FIG. 20 is designed so as to optimize total flow rate by designing a certain flow resistance through the conduit 2000 in accordance with the conditions indicated by the patient. In the case of conduit 2000, this design is preferred at least when patient indications are total or near total proximal coronary artery occlusion.

Figure 21:
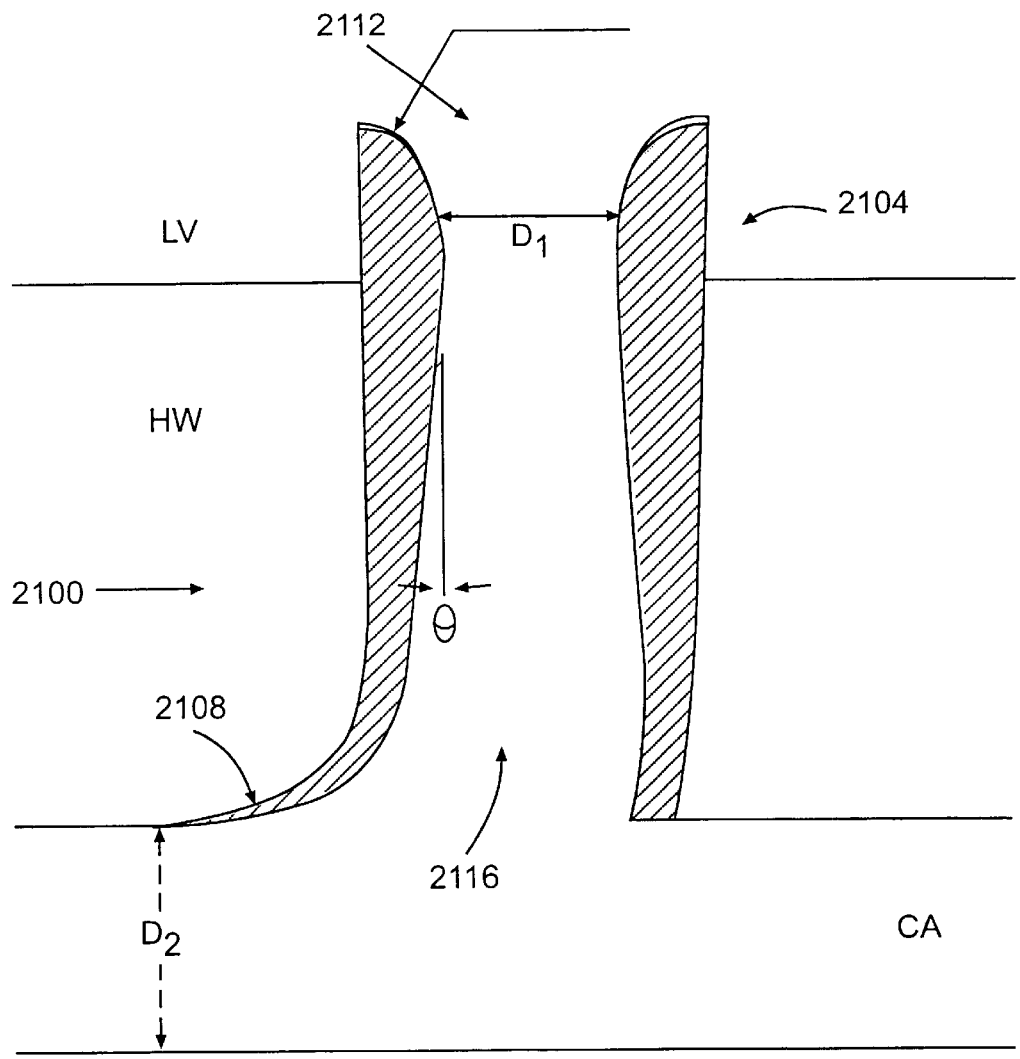
FIG. 21 is a cross-sectional view of another embodiment of a conduit having an it asymmetrical flow resistance with the backward resistance higher than the forward resistance according to an aspect of the invention.

FIG. 21 illustrates a similar embodiment to the conduit of FIG. 20., the conduit 2100 in FIG. 21 having a distal end 2108 that does not extend into the coronary artery CA. For the embodiment of the conduit in FIG. 21, the radius of curvature at the entrance 2108 is approximately ½ of the difference between the diameter $D_2$ of the coronary artery CA and the diameter of the conduit 2100 at the entrance 2112. The advantage in this design is that it does not obstruct flow coming from the partially obstructed artery upstream of the conduit.

Figure 22:
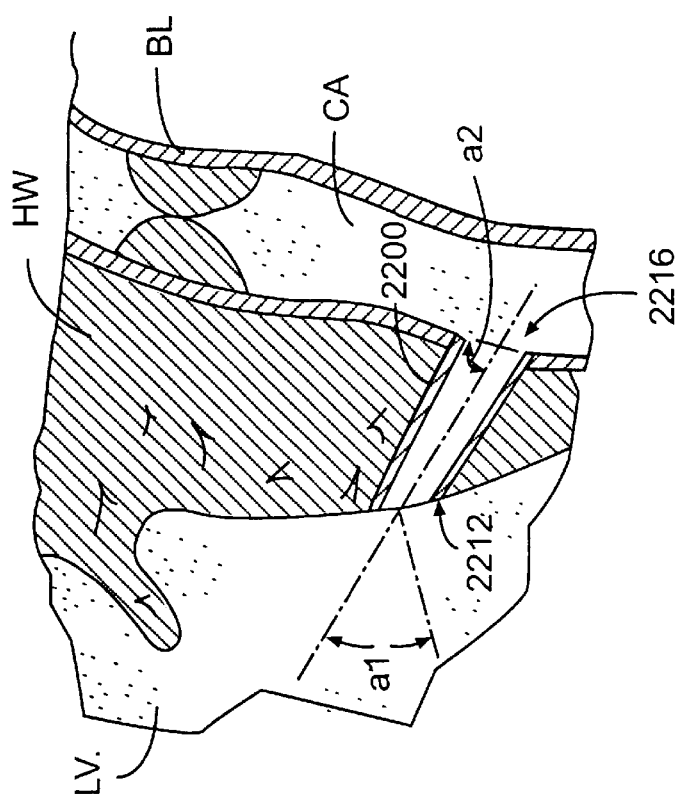
FIG. 22 is a cross-sectional view of yet another embodiment of a conduit having an asymmetrical flow resistance with the backward resistance higher than the forward resistance according to an aspect of the invention.

FIG. 22 illustrates another embodiment in which a conduit 2200, like the conduits described in FIGS. 20 and 21 above, has a proximal end 2212 with a lumen diameter smaller than that at the distal end 2216. In this embodiment, the conduit preferably has a substantially constant wall thickness such that the outer wall and inner wall diameter of the conduit taper in size, preferably in a linear fashion, from the distal end 2216 to the proximal end 2212. The conduit 2200 is provided at an angle in the heart wall to bias blood flow in a downstream direction into the coronary artery CA. More particularly, the conduit is positioned such that its longitudinal axis is at an angle a1 to the perpendicular of the heart wall in the left ventricle, and at an angle a2 to the axis of blood flow in the coronary artery. Angle a2 preferably is an acute angle to bias the blood flow downstream. For example, in one preferred embodiment, the angle a2 may be about 30° to bias blood flow downstream.

Figure 23:
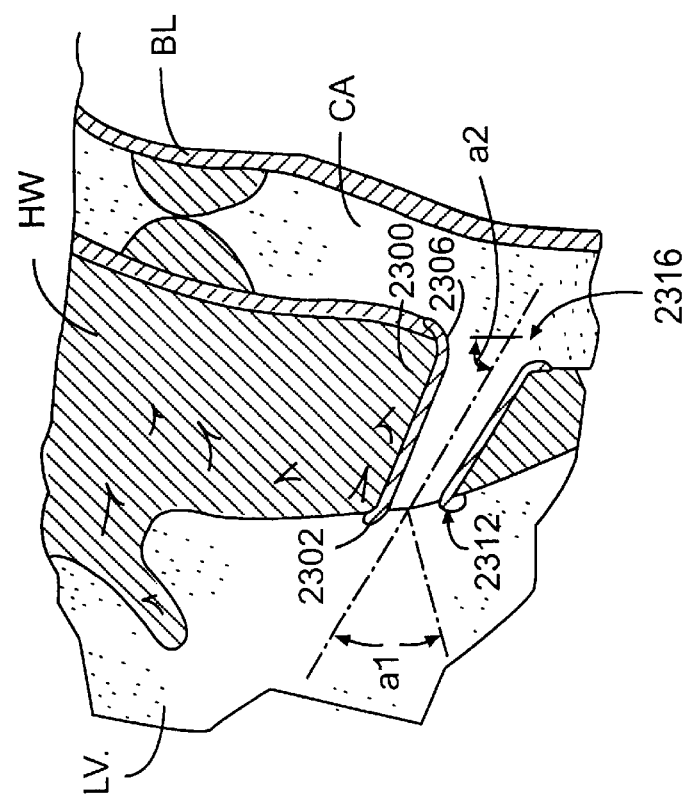
FIG. 23 is a cross-sectional view of an embodiment of a conduit having an asymmetrical flow resistance with the backward resistance higher than the forward resistance according to an aspect of the invention.
Figure 24:
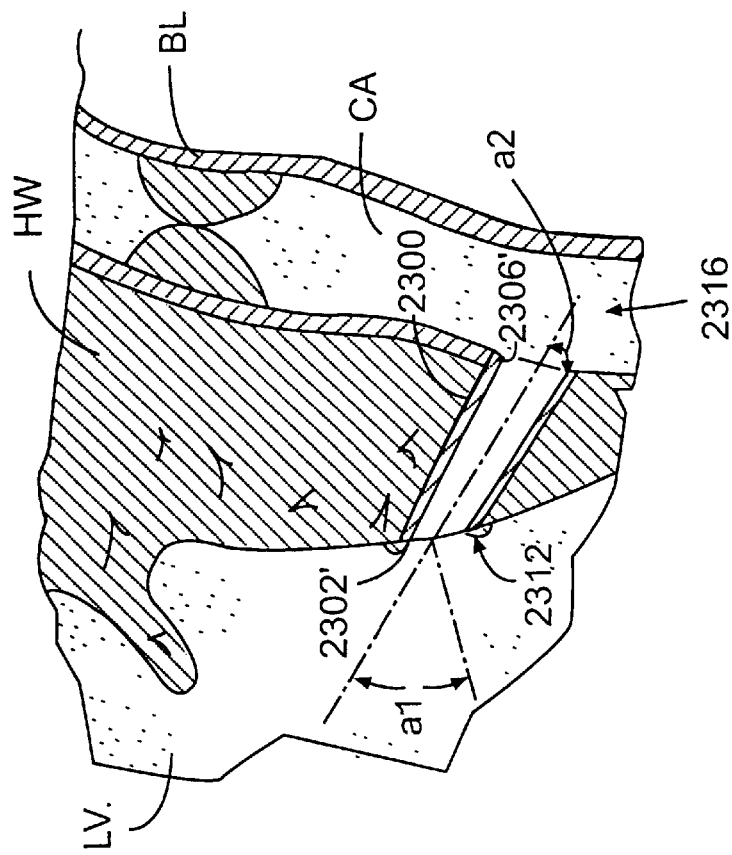
FIG. 24 is a cross-sectional view of another embodiment of a conduit having an asymmetrical flow resistance with the backward resistance higher than the forward resistance according to an aspect of the invention.
Figure 26:
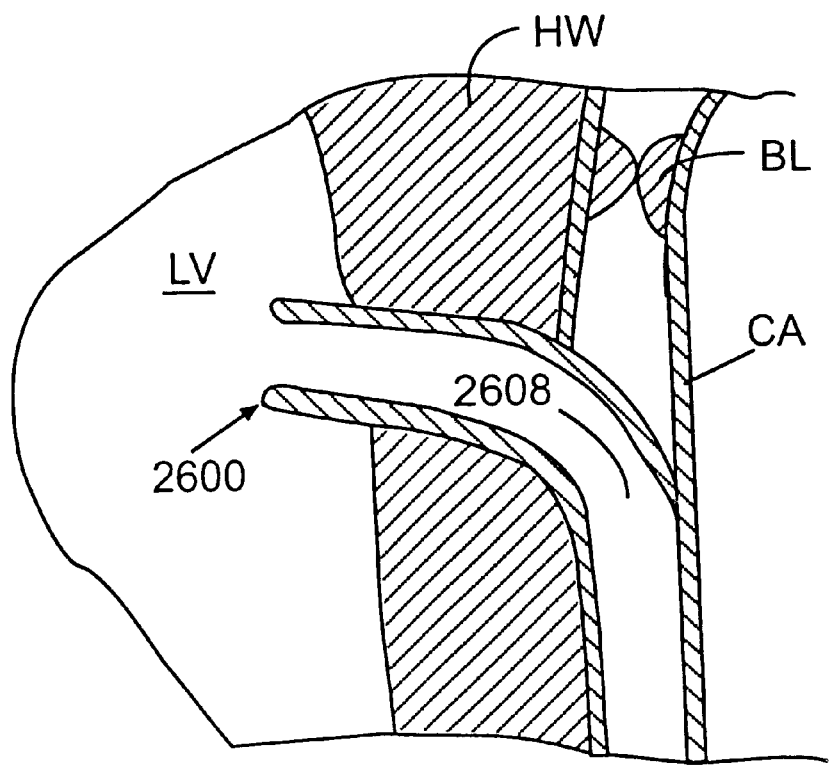
FIG. 26 is a cross-sectional view of yet another embodiment of a conduit having an asymmetrical flow resistance with the backward resistance higher than the forward resistance according to an aspect of the invention.

FIG. 23 illustrates another embodiment in which at least a portion of the conduit and/or the lumen therein is tapered and angled to bias blood flow. Proximal end 2312 of tapered conduit 2300 is further provided with flanges, or bumps, 2302 that extend outward into the ventricle and over the heart wall HW to secure the conduit 2300 to the heart wall. The distal end 2316 is flared such that the end 2306 of the conduit is somewhat rounded and opens nonlinearly outward, and the lumen increases in diameter toward the distal end 2306. In the embodiment shown, the end 2306 does not extend into the coronary artery, although it will be appreciated that in this and other embodiments, such extensions are contemplated. FIG. 24 illustrates another embodiment in which the lumen, after increasing linearly in diameter from the proximal end 2302', maintains a constant diameter or even decreases slightly in diameter near the distal end 2306', while simultaneously curving the blood flow path to bias blood flow downstream into the artery.

Figure 25:
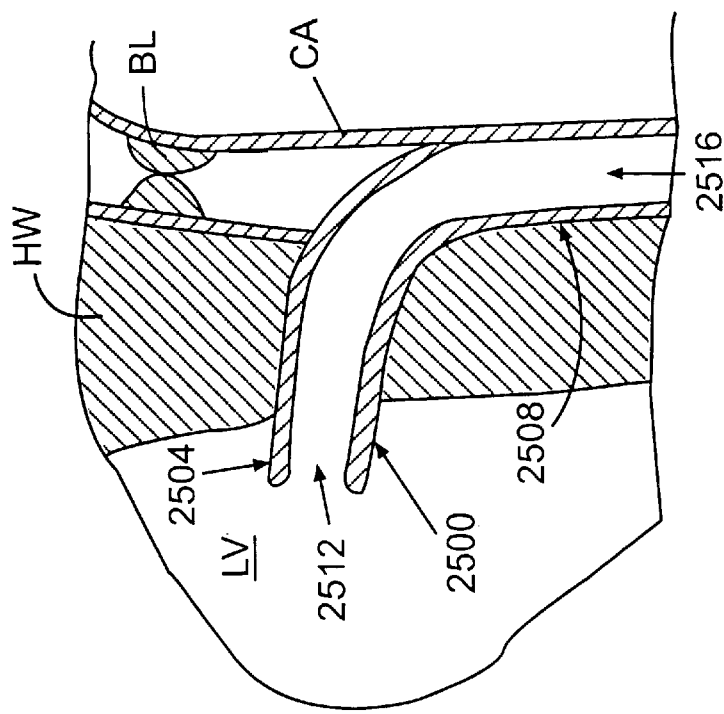
FIG. 25 is a cross-sectional view of an embodiment of a conduit having an asymmetrical flow resistance with the backward resistance higher than the forward resistance according to an aspect of the invention.

FIG. 25 illustrates a further embodiment in which a conduit 2500, such as the conduit 2000 shown in FIG. 20, is disposed in the heart wall at an angle to bias blood flow downstream into the coronary artery CA. The conduit 2500 may have a distal end 2508 that extends into the coronary artery CA, as described above. Alternatively, the distal end 2608 can be substantially coextensive with the heart wall, such as the conduit 2600 shown in FIG. 26.

FIG. 16a, described above with reference to the "Experiments with Various Bypass Conduit Configurations" section, illustrates a conduit 1600 having a proximal end 1602 and a distal end 1604 and a lumen 1606 defined by an inner wall 1608 extending therethrough. The lumen 1606 is designed such that the opening at the proximal end 1602 into the heart chamber or left ventricle LV has a smaller diameter than the opening at the distal end 1604. In one embodiment, the proximal opening has a throat, or inner, diameter of 0.040 inches (1.016 mm) or 0.052 inches (1.3208 mm), and the distal opening has a diameter of about 2 mm. In the embodiment shown, the length of the lumen 1606 between the proximal end and the distal end is about 2 cm. As illustrated, the lumen 1606 preferably tapers and decreases in diameter away from the proximal end 1602. This decrease in lumen diameter is preferably determined by the inner wall 1608 curving concave inward toward the central axis X of the lumen. As illustrated in FIG. 16a, this curvature can be defined by the radius of curvature R, which in one embodiment, is about 0.010 inches (0.254 mm).

After the decrease in diameter away from the proximal end 1602, the lumen diameter preferably increases toward the distal end 1604. More preferably, the lumen diameter increases linearly toward the distal end 1604. As illustrated in FIG. 16a, the increase in diameter is determined by an angle a3 relative to the central axis X of the conduit. In one embodiment, the angle a3 is about 4 degrees.

Although the conduit illustrated in FIG. 16a is shown with a constant wall thickness, it will be appreciated that other conduits having the same or similar inner lumen dimensions are contemplated having other outer wall configurations. For example, the outer wall may have a constant diameter over part or the entire length of the conduit, such as in the embodiments described above. It will also be appreciated that although the proximal end 1602 is shown as being approximately flush with the heart wall in the left ventricle, the conduit may extend into the ventricle as described in the embodiments above. Furthermore, the conduit 1600 is shown in FIG. 16a as being positioned in the heart wall at an angle a4 of about 90 degrees relative to the axis of coronary artery flow. It will be appreciated that the angle a4 may be varied as discussed above to bias blood flow downstream away from the blockage BL.

In the conduit designs of the preferred embodiments, a geometry giving a resistance ratio of ventricle to artery flow of approximately 2 is preferred, as was determined from the lumped parameter model parametric studies. In general, the preferred conduit design makes it harder for fluid to flow toward the ventricle as it is to flow toward the artery. As the experiment results have shown, a conduit of essentially the design of FIG. 16a with a throat diameter of about 0.052 inches at a 90 degree angle of entry a4 to the axis of the coronary artery achieves a flow resistance ratio of approximately 1.2. The same design having a 0.040 inch throat diameter at a 30 degree angle of entry a4 achieved a flow resistance ratio of approximately 1.3. Experimentation has also shown that to maximize the flow ratio, higher overall resistance is desired.

Moreover, a conduit having a constant inner lumen diameter with an angle of entry a4 of about 90 degrees achieved a flow resistance ratio of approximately 1.2. The same conduit provided at an angle of entry a4 of about 30 degrees achieved a flow resistance ratio of approximately 1.4. Thus, decreasing the angle of entry alone can achieve good flow biasing.

Overall, a relatively small diameter at the ventricle will generate considerable turbulence as flow enters the ventricle. Associated with the turbulence is a large loss of energy coupled with a lack of pressure recovery, i.e., pressure at the entry point inside the shunt is approximately equal to ventricular pressure. A gradual taper from the ventricle to the artery is expected to minimize flow separation and turbulence inside the conduit, thereby minimizing the loss of energy and allowing for pressure recovery when flow passes in the forward direction. The taper also leads to high wall shear stresses on back flow and low shear stresses on forward flow, again producing a favorable resistance ratio. Matching the diameters of the conduit and the artery at the artery side of the conduit, and reducing the angle between them also minimizes energy and pressure drops corresponding to forward flow. Using typical estimates of pressure losses associated with the taper, which can be obtained from standard fluid dynamic textbooks (e.g., Fluid Mechanics, Frank M. White, WCB/McGraw Hill, 1999, pp. 370–374) indicates that resistance ratios of about 2 are possible to achieve for bypass conduits in accordance with the present invention. However, such textbook values typically are obtained for conditions in which the flow rates, or Reynold's numbers, are considerably higher and therefore do not correspond directly to the predictions of the current computer simulations or the actual experimental results obtained. This also demonstrates the usefulness of finite element calculations to model the flow through the conduit.

It will be understood that this disclosure, in many respects, is only illustrative. Changes may be made in details, particularly in matters of shape, size, material, number and arrangement without exceeding the scope of the invention. For example, the degree of taper, angle of implantation, diameters of left ventricular and arterial openings, wall thickness, and other similar characteristics of the conduits may be modified depending on such factors as the degree of occlusion of the artery being bypassed and the thickness of the heart wall, for example. Accordingly, the scope of the invention is as defined in the language of the appended claims.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

Appendix A: Detailed Formulation of the Coronary Circulation Analysis

In this section, we present the detailed expressions of the computational procedure to simulate coronary circulation. The schematic diagram of the computational code is represented in FIG. 2.

Variables:
 P: Pressure (unit: mmHg)
 q: Flow rate (unit: ml/sec)
 R: Resistance (unit: mmHg sec/ml=PRU)
 C: Compliance (unit: ml/mmHg)
 D: Diode or check valve
 V: Volume (ml)
Subscripts:
 li: Left ventricle inflow
 lv: Left ventricle
 lo: Left ventricle outflow
 a: Systemic arteries
 st: Stenosis of coronary arteries
 by: Bypass connection from left ventricle
 sh: Shunt connection from left ventricle
 for: Shunt forward direction
 back: Shunt backward direction
 coa: Coronary arterioles
 coc: Coronary capillaries
 imp: Intra-myocardium
 cov: Coronary veins
 eca: Extarcoronary arterioles
 ecv: Extracoronary veins
 ra: Right atrium
 ri: Right ventricle inflow
 rv: Right ventricle
 ro: Right ventricle outflow
 pa: Pulmonary arteries
 pv: Pulmonary veins
 th: Intrathoracic The coronary circulation consists of three compartments: the coronary arteries, the coronary capillaries and the coronary veins. The effects of myocardial muscle contraction or relaxation is produced by temporal variations in the bias pressure $P_{imp}(t)$. The flow rates between the respective compartments are thus $$q_{li} = \begin{cases} (P_{pv} - P_{lv})/R_{pv} & \text{if } P_{pv} > P_{lv} \\ 0 & \text{otherwise} \end{cases} \quad (1)$$

$$q_{lo} = \begin{cases} (P_{lv} - P_a)/R_{lo} & \text{if } P_{lv} > P_a \\ 0 & \text{otherwise} \end{cases} \quad (2)$$

$$q_{st} = (P_a - P_{st})/R_{st} \quad (3)$$

$$q_{sh} = (P_{lv} - P_{st})/R_{sh} \begin{cases} R_{sh} = R_{for} & \text{if } P_{lv} > P_{st} \\ R_{sh} = R_{back} & \text{if } P_{lv} < P_{st} \end{cases} \quad (4)$$

$$q_{coa} = \begin{cases} (P_{coa} - P_{coc})/R_{coa} & \text{if } P_{coa} > P_{coc} \\ \dfrac{(P_{coa} - P_{coc})}{(R_{coa} + \beta/V_{coc}^2)} & \text{otherwise} \end{cases} \quad (5)$$

For the shunt resistance in Eq. 4, the resistance values of the shunt can be changed according to the direction of flow. The forward and backward resistances are shown in FIG. 2. In Eq. 5, the flow rate to capillaries may be either forward (i.e. $q_{coa} > 0$) or retrograde, depending on the sign of the pressure gradient. However, reverse flow ceases as the capillary volume approaches zero since nothing then remains to be squeezed out. Moreover, as the capillary vessels are compressed, their resistance increases and they will throttle the flow. Accordingly, for a negative pressure gradient Eq. 5 reduces backward flow to zero as the capillary volume approaches zero. For flow into the veins and right atrium, a similar approach can be applied, producing the following two equations.

$$q_{coc} = \begin{cases} \dfrac{(P_{coa} - P_{cov})}{(R_{coc} + \beta/V_{coc}^2)} & \text{if } P_{coc} > P_{cov} \\ \dfrac{(P_{coc} - P_{cov})}{(R_{coc} + \beta/V_{cov}^2)} & \text{otherwise} \end{cases} \quad (6)$$

$$q_{cov} = \begin{cases} \frac{(P_{cov} - P_{ra})}{(R_{cov} + \beta/V_{cov}^2)} & \text{if } P_{cov} > P_{ra} \\ \frac{(P_{cov} - P_{ra})}{R_{cov}} & \text{otherwise} \end{cases} \quad (7)$$

$$q_{eca} = (P_a - P_{ecv})/R_{eca} \quad (8)$$

$$q_{ecv} = (P_{ecv} - P_{ra})/R_{ecv} \quad (9)$$

$$q_{ri} = \begin{cases} (P_{ra} - P_{rv})/R_{ri} & \text{if } P_{ra} > P_{rv} \\ 0 & \text{otherwise} \end{cases} \quad (10)$$

$$q_{ro} = \begin{cases} (P_{rv} - P_{pa})/R_{ro} & \text{if } P_{rv} > P_{pa} \\ 0 & \text{otherwise} \end{cases} \quad (11)$$

$$q_{pv} = (P_{pa} - P_{pv})/R_p \quad (12)$$

The state form of the node equations can be written in terms of these flow rates.

(a) Conservation of mass at the left ventricular node yields:

$$q_{li} = q_{lo} + q_{lv} \quad (13)$$

where $$q_{lv} = \frac{d}{dt}[C_l(P_{lv} - P_{th})] = C_l \frac{dP_{lv}}{dt} + (P_{lv} - P_{th}) \quad (14)$$

$$\therefore \frac{dP_{lv}}{dt} = \frac{q_{li} - q_{lo} - (P_{lv} - P_{th}) dC_l(t)/dt}{C_l(t)} \quad (15)$$

(a) At the systemic arteries node:

$$q_{lo} = q_a + q'_a \quad (16)$$

where $$q'_a = C_a \frac{dP_a}{dt} \quad (17)$$

$$\therefore \frac{dP_a}{dt} = \frac{q_{lo} - (q_{st} + q_{eca})}{C_a} \quad (18)$$

(b) At the coronary artery node:

$$q_a + q_{sh} = q_{coa} + q'_{coa} \quad (19)$$

where $$q'_{coa} = C_{coa} \frac{dP_{coa}}{dt} \quad (20)$$

$$\therefore \frac{dP_{coa}}{dt} = \frac{(q_{st} + q_{sh}) - q_{coa}}{C_{coa}} \quad (21)$$

(c) At the coronary capillaries node:

$$q_{coa} = q_{coc} + q'_{coc} \quad (22)$$

where $$q'_{coc} = C_{coc} \frac{d(P_{coc} - P_{imp})}{dt} \quad (23)$$

$$\therefore \frac{dP_{coc}}{dt} = \frac{q_{coa} - q_{coc}}{C_{coc}} + \frac{dP_{imp}}{dt} \quad (24)$$

Capillary volume can be obtained by the relation.

$$V_{coc} = C_{coc}(P_{coc} - P_{imp}) \quad (25)$$

(d) Mass conservation at the coronary veins node:

$$q_{coc} = q_{cov} + q'_{cov} \quad (26)$$

where $$q'_{coc} = C_{cov} \frac{dP_{cov}}{dt} \quad (27)$$

$$\therefore \frac{dP_{cov}}{dt} = \frac{q_{coc} - q_{cov}}{C_{cov}} \quad (28)$$

For the capillary veins, venous pressure is calculated from the pressure-volume relation:

$$P_{cov} = V_{coc} C_{cov}^0 e^{\sigma(V_{cov} - V_{cov}^0)} \quad (29)$$

corresponding to a volume-dependent compliance, defined as the derivative of $V_{cov}$ with respect to $P_{cov}$:

$$C_{cov}(V_{cov}) = \frac{dV_{cov}}{dP_{cov}} = C_{cov}^0(1 + \sigma V_{cov})^{-1} e^{-\sigma(V_{cov} - V_{cov}^0)} \quad (30)$$

Here, $V_{cov}^0$, $C_{cov}^0$ are the reference venous volume and compliance, respectively, and $\sigma$ is the slope of the change in compliance.

(e) Mass conservation at the extra-coronary veins node:

$$q_{eca} = q_{ecv} + q'_{ecv} \quad (31)$$

where $$q'_{ecv} = C_{ecv} \frac{dP_{ecv}}{dt} \quad (32)$$

$$\therefore \frac{dP_{ecv}}{dt} = \frac{q_{ecq} - q_{ecv}}{C_{ecv}} \quad (33)$$

(f) At the right atrium node:

$$q_{cov} + q_{ecv} = q_{ri} + q'_{ra} \quad (34)$$

where $$q'_{ra} = C_{ra} \frac{dP_{ra}}{dt} \quad (35)$$

$$\therefore \frac{dP_{ra}}{dt} = \frac{q_{cov} + q_{ecv} - q_{ri}}{C_{ra}} \quad (36)$$

(g) At the right ventricle node:
By the same procedure with Eq. 15, we can get the equation for the right ventricle node.

$$\frac{dP_{rv}}{dt} = \frac{q_{ri} - q_{ro} - (P_{rv} - P_{th})dC_r(t)/dt}{C_r(t)} \quad (37)$$

(h) At the pulmonary arteries node:

$$\frac{dP_{pa}}{dt} = \frac{q_{ro} - q_{pv}}{C_{pa}} \quad (38)$$

(i) At the pulmonary veins node:

$$\frac{dP_{pv}}{dt} = \frac{q_{pv} - q_{li}}{C_{pv}} \quad (39)$$

Appendix B Parameter Values

| Compartment | $R_{in}$ (PRU) | $R_{out}$ (PRU) | C (ml/mmHg) | $V_0$ (ml) | Sources |
|---|---|---|---|---|---|
| Left heart | 0.01 ($R_{pv}$) | 0.006 | 0.4~10 | 15 | Davis, 1991 |
| Systemic arteries | 0.006 | ($R_{lo}$) | 1.6 | 715 | Davis, 1991 |
| Extra-coronary | ($R_{eac}$) | | 90 | 2450 | Ursino, 1998 |
| Veins | 1.00 | 0.05 ($R_{ri}$) | | | |
| Coronary arteries | ($R_{eav}$) | | | | Schreiner, 1989 |
| Coronary capillaries | | 13.5 | 0.4 | 0.0 | Schreiner, 1989 |
| Coronary veins | (variable) 13.5 | ($R_{coa}$) 1.37 | 0.25 (Variable) | 25 | Schreiner, 1989 |
| Right atrium | ($R_{coa}$) | ($R_{coc}$) | 31.0 | 25 | Ursino, 1998 |
| Right heart | 1.37 | 0.6 ($R_{cov}$) | 1.2~20 | 15 | Davis, 1991 |
| Pulmonary arteries | ($R_{coc}$) | | 4.3 | 90 | Davis, 1991 |
| Pulmonary veins | | 0.0025 ($R_{ra}$) 0.003 | 8.4 | 490 | Davis, 1991 |
| | 0.0025 ($R_{ra}$) 0.003 ($R_{ro}$) 0.08 ($R_{rp}$) | ($R_{ro}$) 0.08 ($R_{rp}$) 0.01 ($R_{pv}$) | | | |
| Stenosis | | Resistance : Variable | | | |
| Bypass resistance | | $R_{by}$ = 0.0001 | | | |
| Intramyocardium Pressure | | $P_{imp}(t) = 0.75 \times P_{LV}(t)$ | | | |
| Total blood volume | | $V_{tot}$ = 5000 ml | | | |
| Reference coronary venous volume | | $V_{cov}^o$ = 25 ml | | | |
| Reference coronary venous volume | | $C_{cov}^o$ = 0.25 ml/mmHg | | | |

REFERENCES

1. Davis, T. D., 1991, "Teaching physiology through interactive simulation of hemodynamics," *MIT M.S. Thesis,* Cambridge, Mass.
2. Ursino, M., 1998, "Interaction between carotid baroregulation and the pulsating heart: a mathematical moedl," *Am., J. Physiol.,* 275, H1733–H1747.
3. Schreiner, W., Neumann, F., and Mohl, W., 1990, "Simulation of coronary circulation with special regard to the venous bed and coronary sinus occlusion," *J. Biomed. Eng,* 12, 429–443.
4. Bathe, K. J., Zhang, H., Wang, M. H., 1995, "Finite Element Analysis of Incompressible and Compressible Fluid Flows with Free Surfaces and Structural Interactions," *Computers and Structures,* 56, No. 2/3, 193–213.
5. Fung, Y. C., 1997, Biomechanics: Circulation, Springer-Verlag, New York.

What is claimed is:

1. A method of bypassing an at least partially occluded blood vessel, comprising:
   determining a resistance to blood flow of the vessel at a location of an at least partial occlusion;
   selecting a conduit having a configuration based on the resistance to blood flow of the vessel at the location of the at least partial occlusion; and
   implanting the conduit in a heart wall between a heart chamber and the vessel downstream of the at least partial occlusion to directly flow blood between the chamber and the vessel.

2. The method of claim 1, wherein the selecting includes selecting a conduit having a higher resistance to blood flow in a direction from the vessel to the chamber than in a direction from the chamber to the vessel when the resistance to blood flow of the vessel at the location of the at least partial occlusion ranges from approximately 45 mmHg sec/ml to 76 mmHg sec/ml.

3. The method of claim 1, wherein the vessel is an artery.

4. The method of claim 3, wherein the chamber is a left ventricle.

5. A heart implant for bypassing an at least partially occluded blood vessel, the implant comprising:
   a first end defining a vessel opening configured to be placed in flow communication with a blood vessel;
   a second end opposite the first end and defining a chamber opening that is smaller than the vessel opening and configured to be placed in flow communication with a heart chamber; and
   a wall extending between the first and second ends defining a lumen extending from the vessel opening to the chamber opening, wherein said ends and said wall are configured such that the implant has a greater resistance to blood flow in a first direction from the vessel opening to the chamber opening than in a second direction from the chamber opening to the vessel opening, and wherein the implant is configured to be positioned in the heart such that the second end is closer to the heart chamber than the first end is to the heart chamber.

6. The implant of claim 5, wherein the implant is configured to be positioned in a heart wall, and wherein the vessel opening is configured to be placed in flow communication with the blood vessel at a location downstream from an occlusion.

7. The implant of claim 5, wherein the chamber opening is configured to be placed in flow communication with a left ventricle.

8. The implant of claim 7, wherein the vessel opening is configured to be placed in flow communication with a coronary artery.

9. The implant of claim 5, wherein the vessel opening is configured to be placed in flow communication with a coronary artery.

10. The implant of claim 5, wherein a ratio of resistance to blood flow through the implant from the vessel to the chamber to resistance to blood flow through the implant from the chamber to the vessel is greater than approximately 1.1.

11. The implant of claim 5, wherein a ratio of resistance to blood flow through the implant from the vessel to the chamber to resistance to blood flow through the implant from the chamber to the vessel is approximately 2.

12. The implant of claim 5, wherein the vessel has a resistance to blood flow of at least approximately 45 mmHG sec/ml to approximately 76 mmHG sec/ml at a location of an occlusion.

13. The implant of claim 5, wherein the vessel opening is configured to be placed in flow communication with the at least partially occluded blood vessel.

14. A heart implant for bypassing an at least partially occluded blood vessel, comprising:

a first end defining a vessel opening configured to be placed in flow communication with a blood vessel;

a second end opposite the first end and defining a chamber opening that is smaller than the vessel opening and is configured to be placed in flow communication with a heart chamber; and a wall extending between the first and second ends defining a lumen extending from the vessel opening to the chamber opening, wherein the implant is configured to have a greater resistance to blood flow in a first direction from the vessel opening to the chamber opening than in a second direction from the chamber opening to the vessel opening without any active flow control mechanism, and wherein the implant is configured to be positioned in the heart such that the second end is closer to the heart chamber than the first end is to the heart chamber.

15. The implant of claim 14, wherein the implant is configured to be positioned in a heart wall, and wherein the vessel opening is configured to be placed in flow communication with the blood vessel at a location downstream from an occlusion.

16. The implant of claim 14, wherein the chamber opening is configured to be placed in flow communication with a left ventricle.

17. The implant of claim 16, wherein the vessel opening is configured to be placed in flow communication with a coronary artery.

18. The implant of claim 14, wherein the vessel opening is configured to be placed in flow communication with a coronary artery.

19. The implant of claim 14, wherein a ratio of resistance to blood flow through the implant from the vessel to the chamber to resistance to blood flow through the implant from the chamber to the vessel is greater than approximately 1.1.

20. The implant of claim 14, wherein a ratio of resistance to blood flow through the implant from the vessel to the chamber to resistance to blood flow through the implant from the chamber to the vessel is approximately 2.

21. The implant of claim 14, wherein the vessel has a resistance to blood flow of at least approximately 45 mmHG sec/ml to approximately 76 mmHG sec/ml at a location of an occlusion.

22. The implant of claim 14, wherein the vessel opening is configured to be placed in flow communication with the at least partially occluded blood vessel.

23. A method for bypassing an at least partially occluded blood vessel, the method comprising:

providing an implant having a first end defining a vessel opening, a second end defining a chamber opening, and a wall defining a lumen extending from the vessel opening to the chamber opening, the chamber opening being smaller than the vessel opening; and placing the vessel opening in flow communication with a blood vessel and the chamber opening in flow communication with a heart chamber, such that the second end is closer to the heart chamber than the first end is to the heart chamber and blood flows through the implant between the heart chamber and the blood vessel;

wherein the ends and the wall are configured such that the implant has a greater resistance to blood flow in a first direction from the vessel opening to the chamber opening than in a second direction from the chamber opening to the vessel opening.

24. The method of claim 23, further comprising positioning the implant in a heart wall.

25. The method of claim 23, wherein placing the vessel opening includes placing the vessel opening in flow communication with the blood vessel at a location downstream from an occlusion.

26. The method of claim 23, wherein placing the chamber opening includes placing the chamber opening in flow communication with a left ventricle.

27. The method of claim 26, wherein placing the vessel opening includes placing the vessel opening in flow communication with a coronary artery.

28. The method of claim 23, wherein placing the vessel opening includes placing the vessel opening in flow communication with a coronary artery.

29. The method of claim 23, wherein a ratio of resistance to blood flow through the implant from the vessel to the chamber to resistance to blood flow through the implant from the chamber to the vessel is greater than approximately 1.1.

30. The method of claim 23, wherein a ratio of resistance to blood flow through the implant from the vessel to the chamber to resistance to blood flow through the implant from the chamber to the vessel is approximately 2.

31. The method of claim 23, wherein the vessel has a resistance to blood flow of at least approximately 45 mmHG sec/ml to approximately 76 mmHG sec/ml at a location of an occlusion.

32. The implant of claim 23, wherein placing the vessel opening includes placing the vessel opening in flow communication with the at least partially occluded blood vessel.

33. A method for bypassing an at least partially occluded blood vessel, the method comprising:

providing an implant having a first end defining a vessel opening, a second end defining a chamber opening, and a wall defining a lumen extending from the vessel opening to the chamber opening, the chamber opening being smaller than the vessel opening; and placing the vessel opening in flow communication with a blood vessel and the chamber opening in flow communication with a heart chamber, such that the second end is closer to the heart chamber than the first end is to the heart chamber and blood flows through the implant between the heart chamber and the blood vessel;

wherein the implant is configured to have a greater resistance to blood flow in a first direction from the vessel opening to the chamber opening than in a second direction from the chamber opening to the vessel opening without any active flow control mechanism.

34. The method of claim 33, further comprising positioning the implant in a heart wall.

35. The method of claim 33, wherein placing the vessel opening includes placing the vessel opening in flow communication with the blood vessel at a location downstream from an occlusion.

36. The method of claim 33, wherein placing the chamber opening includes placing the chamber opening in flow communication with a left ventricle.

37. The method of claim 36, wherein placing the vessel opening includes placing the vessel opening in flow communication with a coronary artery.

38. The method of claim 33, wherein placing the vessel opening includes placing the vessel opening in flow communication with a coronary artery.

39. The method of claim 33, wherein a ratio of resistance to blood flow through the implant from the vessel to the chamber to resistance to blood flow through the implant from the chamber to the vessel is greater than approximately 1.1.

40. The method of claim 33, wherein a ratio of resistance to blood flow through the implant from the vessel to the chamber to resistance to blood flow through the implant from the chamber to the vessel is approximately 2.

41. The method of claim 33, wherein the vessel has a resistance to blood flow of at least approximately 45 mmHG sec/ml to approximately 76 mmHG sec/ml at a location of an occlusion.

42. The implant of claim 33, wherein placing the vessel opening includes placing the vessel opening in flow communication with the at least partially occluded blood vessel.

* * * * *